(12) United States Patent
Saban et al.

(10) Patent No.: US 6,790,341 B1
(45) Date of Patent: Sep. 14, 2004

(54) MICROBAND ELECTRODE ARRAYS

(75) Inventors: Steven Saban, Snohomish, WA (US); Robert B. Darling, Lake Forest Park, WA (US); Paul Yager, Seattle, WA (US)

(73) Assignee: University of Washington, Seattle, WA (US)

( * ) Notice: Subject to any disclaimer, the term of this patent is extended or adjusted under 35 U.S.C. 154(b) by 225 days.

(21) Appl. No.: 09/650,075

(22) Filed: Aug. 29, 2000

Related U.S. Application Data

(63) Continuation of application No. 08/963,678, filed on Oct. 31, 1997, now Pat. No. 6,110,354.
(60) Provisional application No. 60/030,319, filed on Nov. 1, 1996.

(51) Int. Cl.[7] .............................................. G01N 27/26
(52) U.S. Cl. ...................................... 205/775; 205/789
(58) Field of Search ........................... 204/434, 403.13, 204/416, 409; 205/775, 789

(56) References Cited

U.S. PATENT DOCUMENTS

| | | | |
|---|---|---|---|
| 3,530,046 A | | 9/1970 | Mochizuki et al. |
| 4,874,500 A | | 10/1989 | Madou et al. ............... 204/412 |
| 5,103,179 A | | 4/1992 | Thomas et al. ............. 324/438 |
| 5,120,421 A | | 6/1992 | Glass et al. .................. 204/406 |
| 5,194,133 A | * | 3/1993 | Clark et al. ............ 204/403.01 |
| 5,217,112 A | | 6/1993 | Almon ..................... 204/153.1 |
| 5,254,235 A | | 10/1993 | Wu ............................ 204/284 |
| 5,292,423 A | | 3/1994 | Wang ......................... 204/434 |
| 5,296,125 A | | 3/1994 | Glass et al. ............. 204/153.21 |
| 5,378,343 A | | 1/1995 | Kounaves et al. .......... 204/413 |
| 5,393,399 A | | 2/1995 | Van den Berg et al. ..... 204/412 |
| 5,407,554 A | * | 4/1995 | Sauer ......................... 204/403 |
| 5,437,772 A | * | 8/1995 | De Castro et al. .......... 205/775 |
| 5,437,999 A | | 8/1995 | Diebold et al. ............. 435/288 |
| 5,460,710 A | * | 10/1995 | Williams et al. ....... 204/290.01 |
| 5,580,435 A | * | 12/1996 | Kovacs ........................ 204/451 |
| 5,670,031 A | | 9/1997 | Hintsche et al. ............. 204/412 |
| 5,676,820 A | | 10/1997 | Wang et al. .............. 205/777.5 |
| 5,873,990 A | * | 2/1999 | Wojciechowski et al. ... 204/406 |
| 5,958,215 A | * | 9/1999 | Kuhr et al. .................. 204/400 |
| 6,045,676 A | * | 4/2000 | Mathies et al. .............. 204/601 |
| 6,110,354 A | * | 8/2000 | Saban et al. ................. 205/775 |

FOREIGN PATENT DOCUMENTS

WO  9510040 A1 * 4/1995

OTHER PUBLICATIONS

Guerin, L.J. et al. (1997), Simple and low cost fabrication of embedded microchannels by using a new thick-film photoplastic, Jun. 16–19, 1997, Proc. Intl. Conf. On Solid state Actuators Workshop, Chicago, IL IEEE 2:1419–1421.*
Bond, A.M. et al. (1986), "Theory and Experimental Characterization of Linear Gold Microelectrodes with Submicrometer Thickness," J. Phys. Chem. 90:2911–2917.
Chen, J. and Wise, K.D. (1994), "A multichannel neural probe for selective chemical delivery at the celluar level," Jun. 13–16, 1994, Proc. Solid State Sensors and Actuators Workshop, Hilton Head, SC, IEEE, pp. 256–259.

(List continued on next page.)

Primary Examiner—Alex Noguerola
(74) Attorney, Agent, or Firm—Greenlee, Winner and Sullivan, P.C.

(57) ABSTRACT

The present invention provides microband electrode array sensors for detecting the presence and measuring the concentration of analytes in a sample. The microband electrodes of the invention have both a width and thickness of microscopic dimensions. Preferably the width and thickness of the microbrand electrodes are less than the diffusion length of the analyte(s) of interest. In general, both the thickness and width of the electrodes are less than about 25 micrometers. The electrodes are separated by a gap insulating material that is large enough that the diffusion layers of the electrodes do not overlap such that there is no interference and the currents at the electrodes are additive. Microband electrode arrays of this invention exhibit true steady-state amperometric behavior.

36 Claims, 17 Drawing Sheets

OTHER PUBLICATIONS

Kovach, P.M. et al. (1985), "Faradaic electrochemistry at microcylinder, band, and tubular band electtodes," J. Electroanal. Chem. 185:285–295.

Morris, R.B. et al. (1987), "Electrochemistry at Pt band electrodes of width approaching moecular dimensions. Breakdown of transport equation at very smll electrodes," J. Phys. Chem. 91;3559–3564.

Sobek, D. et al. (1994), "Microfabricated fused silica flow chambers for flow cytometry," Jun. 13–16, 1994, Proc. Solid State Sensors and Actuators Workshop, Hilton Head, SC, IEEE, pp. 260–263.

Tallman, D.E. (1994), "Square wave voltammetry of reversible systems at ring microelectrodes," Anal. Chem. 66:557–565 Feb.

Thormann, W. et al., (1985) "Voltammetry at linear gold and platinum microelectrode arrays produced by lithographic technqiues," Anal. Chem. 57:2764–2770 Dec.

Wehmeyer, K.R. et al. (1985), "Electroanalytical properties of band electrodes of submicrometer width," Anal. Chem. 57:1913–1916 Aug.

Wightman, R.M. and Wipf, D.O. (1989), "Voltammertry at ultramicroelectrodes" Electroanal. Chem. 15:267–353.

Woolley, A.T. and Mathies, R.a. (1994), "Ultra–high–speed DNA fragment separations using microfabricated capillary array electrophoresis chips," Proc. Natl. Acad. Sci. USA 91:11348–11352 Nov.

* cited by examiner

— Pt band array (10 electrodes)

♦ Pt band array (24 electrodes)

MICROBAND ELECTRODE ARRAYS

CROSS-REFERENCE TO RELATED APPLICATIONS

This application is a continuation of U.S. Ser. No. 08/963,678, filed Oct. 31, 1997, now U.S. Pat. No. 6,110,354, which is incorporated herein in its entirety to the extent not incompatible herewith and claims the benefit of priority under 35 U.S.C. 119(e) of U.S. provisional application Serial No. 60/030,319 filed on Nov. 1, 1996 and which is also incorporated by reference herein in its entirety.

STATEMENT REGARDING FEDERALLY SPONSORED RESEARCH OR DEVELOPMENT

The U.S. Government may have rights in this invention based on grant support from National Science Foundation Grant No. EEC9418532AM07.

BACKGROUND OF THE INVENTION

Testing of various types of samples, for example, drinking water, waste water, and biological fluids such as blood and urine, can be performed electrochemically. Assessment of water quality for human health, environmental, and industrial concerns has become increasingly important over the past few decades. Analysis of pollutants, e.g., trace metals in aqueous solution is particularly important because many of these metals (e.g., Hg, Pb) are toxic in low concentrations.

Microelectrodes are useful in analysis of fluids containing electro-active analytes, particularly metals. Microelectrodes can have various geometries, e.g., hemispheres, disks, bands, tubes, rings, and cylinders and generally have one or more dimension on the order of 0.1 to 20 micrometers (Morris, R. B., Franta, D. J. and White, H. S. J. Phys. Chem. 1987, 91, 3559–3564). A microelectrode is an electrode with a dimension (thickness, T or width, W or radius, r) substantially less than the characteristic diffusion length of an analyte of interest. The characteristic diffusion length of an analyte is a function of the duration of the measurement, i.e., it is the square root of the product of the analyte's diffusion coefficient multiplied by the time of the measurement. As is known to those in the art, small metal cations, for example, have typical diffusion lengths which range from about 0.1 to about 1 $cm^2$/second, depending, of course, on ionic mobility, among other factors.

As the dimensions of an electrode are made smaller, a number of advantages are gained. The mass transport rate increases, the electrode surface is covered more uniformly, diffusion layer capacitance decreases, the effects of solution resistance decrease, the signal to noise ratio increases, and the need for supporting electrolyte and deoxygenation of the sample is reduced or obviated.

The signal from microelectrodes consists of two components: a faradaic component 25 and a non-faradaic component. The faradaic component represents a chemical reaction occurring on the electrode surface. The non-faradaic component represents the capacitive charging unrelated to the chemistry occurring on the electrode surface. The faradaic component is usually proportional to the periphery of the electrode. The non-faradaic component is proportional to the surface area of the electrode. Electrode geometries which maximize the periphery to surface area ratio also maximize the ratio of the faradaic component to the non-faradaic component and produce readily producible signal. Microelectrodes produce higher periphery to area ratios. The area contacting the sample determines the non-faradaic component, while the periphery determines the faradaic (desired) component.

U.S. Pat. No. 5,120,421 teaches that conventionally sized electrodes often have large uncompensated resistance, making them useless in solutions of low conductivity, e.g., for detecting very low concentrations of analytes.

The diffusion layer (boundary layer), as will be understood by those of ordinary skill in the art, is that volume of fluid sample between where the analyte is at bulk concentration and where the analyte concentration approaches zero (i.e., the fluid layer immediately adjacent to the analyte-covered electrode). It is known to those in the art that the diffusion layer is related to the capacitance of the electrode and the non-faradaic component of the signal, and the diffusion layer can be measured with an electrocapacitance meter (A. Bard and L. R. Faulkner, *Electrochemical Methods: Fundamentals and Applications*, John Wiley, (1980); and P. t. Kissinger and W. Heineman, Eds., *Laboratory Techniques in Electroanalytical Chemistry*, 2nd ed., Marcell Dekker, (1990) which are incorporated in its entirety by reference herein). Hence, the diffusion layer acts as a capacitor and any change in applied voltage produces non-faradaic current (component that interferes with the signal). Decreasing the size (dimensions) of the electrode leads to a decrease in the charge stored in the diffusion layer because the electrode surface area is decreased.

The only disadvantage of microelectrodes is the difficulty in measuring low currents. This problem can be overcome by fabrication of an array of identical microelectrodes, so that current signals from multiple microelectrodes can be added together to make a large enough signal for accurate measurements to be made. If the individual electrodes are spaced sufficiently far apart from one another, the currents from each individual electrode are additive and non-interfering.

In recent years many attempts have been made to develop more useful electrode sensors, some with multiple electrodes (arrays) and some with microelectrodes, and methods for making them. U.S. Pat. No. 5,437,999 by Diebold et al. describes an electrode sensor and methods for making such a sensor. The method utilizes photolithographic and screen-printing techniques.

U.S. Pat. No. 5,393,399 by Van den Berg et al. describes an amperometric sensor having a planar structure obtained by photolithographic techniques, useful for measuring the content of an oxygen reducible substance in a fluid.

U.S. Pat. No. 5,670,03 by Hintsche et al. describes an electrochemical sensor with multiple interdigital microelectrodes with structure widths * in the sub-micron range. The spaces between the interdigitated electrodes is about 700 nm, "which are small relative to the distances traveled by the molecules to be detected, in the measuring time."

U.S. Pat. No. 5,217,112 by Almon describes an electrode sensor comprising an auxiliary electrode, a reference electrode and five working electrodes, methods for making such a sensor and voltammetric methods of using such a sensor.

U.S. Pat. No. 5,437,772 by De Castro et al. describes an electrode sensor with multiple interdigitated electrodes which can be coated with mercury forming an array useful for trace metal analysis of samples, especially those containing lead. The sensor is particularly useful in anodic stripping voltammetry techniques.

U.S. Pat. No. 5,103,179 by Thomas et al. describes a water analyzer having several electrodes of the type which normally interfere with one another (active and passive sensors). The water analyzer includes a first electrode (active) which perturbs the sample solution, a second electrode whose reading is affected by the operation of the first electrode, and a sequencing means which activates the first electrode at a time different from the reading of the second electrode.

U.S. Pat. No. 4,874,500 by Madou et al. describes a microelectrochemical electrode structure wherein a monolithic substrate has a well extending into the substrate from the front surface and a passage extending into the substrate from the back surface to the bottom of the well, and an electrode wholly between the front and back surfaces, and a conductor in the passage for electrically communicating the electrode to the back surface.

U.S. Pat. Nos. 5,296,125 and 5,120,421 by Glass et al. describe an electrochemical detection system including a multielement microelectrode array detector capable of acquiring a plurality of signals and electronic means for receiving these signals and converting them into a readout or display providing information about the nature and concentration of elements present in the sample solution.

U.S. Pat. No. 5,676,820 by Wang et al. describes an electrochemical sensor for remote detection, particularly useful for metal contaminants and organic or other compounds. The microelectrode is connected to a long communications cable, allowing convenient measurements of samples as far away as ten to more than 100 feet.

U.S. Pat. No. 5,292,423 by Wang describes a method and apparatus for trace metal testing using mercury-coated screen printed electrodes. Voltammetric and potentiometric stripping analyses are used. Screen printing allows for formation of electrodes with smallest dimensions of about 25 micrometers.

U.S. Pat. No. 5,254,235 by Wu describes a microelectrode array, contructed from a woven a minigrid, preferably comprising multiple microdisks. The minigrid is formed by a plurality of vertical and horizontal conductive filaments woven together, wherein the horizontal elements are parallel to the exposed surface of the substrate and the vertical elements extend parallel to the longitudinal axis of the electrode. The microelectrode array is formed by potting the minigrid in an electrically insulating material, such as epoxy resin. The ends of the vertical elements are exposed at the mesuring end surface by grinding away an outer layer of the substrate such that the end-surface and vertical filament ends define a measuring surface for the microelectrode. The filaments are preferably cylindrical. The typical thickness of the minigrids range from about 3 micrometers to about 6 micrometers. The spacing between the microdisks may be selected to minimize adverse effects resulting from overlapping diffusion layer areas surrounding each of the microdisks.

None of the above references, nor any reference known to the present inventors, describes an array of microband electrodes which gives true steady-state current. That is, there has been no apparatus or method for making an apparatus having an array of microband electrodes with adequate dimensions and spacing such that the individual microband electrodes do not interfere with one another.

As is understood by those of ordinary skill in the art and as detailed in U.S. Provisional Application Serial No. 60/030,319, spherical (disks)-and hemispherical microelectrodes exhibit chronoamperometric steady-state behavior in relatively short periods of time. Semi-infinite planar electrodes (i.e., those with sufficiently large surface areas that edge effects are negligible) exhibit Cottrellian chronoamperometric behavior: the current approaches zero at long times (not steady-state, as the current would be with a microdisk).

Diffusion to microdisks and semi-infinite planar electrodes is not uniform. The flux of analyte to the electrode surface occurs primarily at the outer circumference and edges, respectively. The central portion of the electrode is relatively free of analyte while the edges contain the bulk of the deposited analyte. This behavior has prompted the design and fabrication of small ring electrodes (microelectrodes) which exhibit chronoamperometric behavior similar to that of microdisks (steady-state), but with improved signal to noise ratios (Tallman, D. E. *Anal. Chem.*, 1994, 66:557). These electrodes suffer from limits on the thickness of the ring (about 2 microns) based on the wavelength of the light source used in the photolithography used to make them.

An alternative to ring microelectrodes is a band microelectrode (microelectrodes which are rectangular or square in shape).

The prior art teaches that the amperometric behavior of microband electrodes is quasi-steady-state. The limiting current, it has been understood by those in the art, decays as a function of time but not a fast as true Cottrellian behavior (as does an infinite planar electrode), but it doesn't reach a steady-state (like a hemisphere or disk microelectrode) either.

U.S. Pat. No. 5,254,235 by Wu, mentioned above, explains that the failure to obtain true steady-state microelectrode arrays "comes from the fact that either the individual electrodes themselves exhibit only virtual steady-state current because of their size, such as microband electrodes, or the disks are randomly dispersed with separations therebetween that are too small causing current shielding." (Virtual steady-state is equivalent to quasi-steady-state.)

Morris, R. B;, Frahta, D. J. and White, H. S. in *J. Phys. Chem.*, 1987, 91:3559 describe a band microelectrode in which the thickness of the band can be as thin as 200 angstroms, made by either thermal or electron beam evaporation sources and a crystal monitor to control the thickness of the deposited film. The microband electrodes in this reference were made of platinum and gold. The width (W) of the microelectrodes was between 0.5 and 1 cm, and the thickness (T) between 20 and 500 angstroms. As the authors of the reference explain, "since the gap width of any break in the band electrode is insignificant compared with the length of any one segment, and since each segment is in electrical contact with the bulk surface film, the overall geometry approximates that of a single band of known macroscopic length."

Early attempts to describe the diffusion to microband electrodes used a hemicylindrical geometry to describe the edge of the band (Wehmeyer, K. R., Deakin, M. R., and Wightman, R. M. *Anal. Chem.*, 1985, 57:1913; Kovach, P. M., Caudill, W. L., Peters, D. G. and Wightman, R. M. *J. Electroanal. Chem.*, 1985, 185:285). These two references describe microband electrodes with dimensions of 5–2300 nanometers thickness by (macroscopic) centimeters width, and about 18 microns by (macroscopic) about 0.32 centimeters width, respectively. Both of these papers teach that microbands exhibit quasi-steady-state amperometric behavior.

All of the above mentioned microband electrodes have small widths but very much larger, macroscopic lengths. The advantages of the band geometry result from the high magnitude of the current because of the long length, coupled with high mass transport diffusion rate because of the very small width.

The theory regarding microband behavior, i.e. that microbands exhibit quasi-steady state behavior at long times, is based on the assumption that the width of the band is macroscopic. Thus, at long times, the behavior of a microband electrode is dominated by semi-infinite planar diffusion.

Thormann, W., van den Bosch, P., and Bond, A. M. (*Anal. Chem.*, 1985, 57:2764) fabricated an array of Au microband structures in which both dimensions were in the microelectrode regime (T=0.1 μm, W=15 μm). The spacing of these electrodes, however, was only 30 μm apart. This results in a θ) value of 0.75 which could lead to overlap of individual diffusion layers at short periods of time. This would manifest itself as a semi-infinite diffusion response and therefore the limiting current would not achieve a true steady state. Additionally, tests on these electrodes involved cyclic voltammograms only and not any chronoamperometric measurements.

BRIEF SUMMARY OF THE INVENTION

The present invention provides a microband electrode array sensor for detecting the presence and measuring the concentration of analytes in a sample. The microband electrodes of the present invention have both a width and a thickness of microscopic dimensions. Preferably the width and thickness of the microband electrode are less than the diffusion length of the analyte(s) of interest. Generally, the width and thickness of the microband electrode are less than about 25 micrometers. Gaps between adjacent microband electrodes are large enough that the diffusion layers do not overlap, thereby providing for true steady-state amperometric behavior. The present invention provides a microband electrode array which, contrary to prior-art teaching, shows true steady-state behavior. Steady-state behavior is shown when a chronoamperometric measurement (current versus time) displays a horizontal asymptote, i.e. the current measured does not substantially change with time after equilibration.

The sensor of the present invention is easily fabricated and can be made in bulk quantities conveniently using batch-processing methods. Additionally, the sensor can be re-used multiple times, as its microband electrodes are polishable.

The present sensor includes a substrate having a first edge; a plurality of electrodes are between the substrate and a layer of insulating material, the layer of insulating material having a first edge; the first edge of the substrate and the first edge of the insulating material are aligned, either by polishing or by cleaving off the end of the sensor, to form a single edge; the microband electrodes are exposed at the single edge; and the insulating material forms a plurality of gaps, one gap between each of two adjacent microband electrodes and each of the gaps having a length greater than the diffusion layer formed during operation of the sensor. The exposed tips of the electrodes are the active (working) surface of the electrodes, i.e. the microband electrodes.

Preferably, photolithographic techniques are used to fabricate the microband electrodes. Thin film evaporation, sputtering and chemical vapor deposition allow for deposition of very thin layers of electrically conductive material, i.e. microband electrodes with very small widths. With photolithography, a plurality of electrodes with precisely controlled dimensions is deposited and pattterned on a substrate which is then coated with a layer of insulating material. Although the thickness of the microband electrode can vary greatly, the thickness of the electrode (and thus microband electrode) can be easily controlled to within about 20 Å. The electrode tips are exposed and preferably made flush with the edge of the substrate and insulating material either by polishing or by cleaving off the end of the sensor. If the tips are not substantially flush, for example, it the tips are recessed or if the tips extend farther than the edge of the substrate and insulating material, then particles may become entrapped, in the recesses or in eddies behind the tips, respectively, causing fouling of the sensor. Preferably, the end of the sensor is polished so that it is smooth to within about 0.03 micrometers to about 0.06 micrometers.

The term "plurality," as used herein refers to two or more. The term "analytes," as used herein, refers to electro-active species, both organic and inorganic, neutral and ionic, particularly metals and metal ions.

In a preferred embodiment, referred to herein as the planar embodiment, the sensor includes a planar substrate, one which is insulating on its outer surface, upon which are deposited stripes of electrically conductive material, i.e. the electrodes, which are preferably chosen from the platinide (noble) metals, noble metal alloys, transition metals and carbon. Planar substrates include conductive substrates coated with an insulating layer. Examples of planar substrates include but are not limited to a sheet of glass, block of plastic or an oxidized silicon wafer. Mercury electrodes can also be used and are fabricated by plating a coating of mercury onto a pre-existing electrode, e.g., platinum, carbon and preferably iridium electrodes (U.S. Pat. No. 5,378,343 by Kounaves and Kovacs). The term "planar substrate," as used herein, refers to a substrate which is substantially flat and continuous, like a slab of plastic or piece of glass.

Each electrode can be thought of as having three parts, each part in electrical connection with the other parts: (1) the interconnect stripe, which tapers away from a bonding pad; (2) the electrode base, which does not taper and is connected to the interconnect stripe; and (3) the microband electrode, which is the tip of the electrode base. The interconnect stripe is electrically connected, e.g., via a metal wire, to the bonding pad or other means for conducting the measured signal from each electrode to a recording device. The interconnect stripes taper in width from the end near the bonding pad toward the microband electrode (tip), but the tapering ends before the tip. The non-tapered portion of the electrode is referred to herein as the electrode base. The interconnect stripes and bonding pads can also be fabricated by photolithograpy and they can be: (1) the same metal or material as the electrode base and microband electrodes, and fabricated simultaneously, or (2) a different metal or material than the electrode base and microband electrodes, and fabricated prior or subsequent to fabrication of microband electrodes. The electrode base and microband electrode are, of course, the same material, as the microband electrode is the tip of the electrode base. A layer of insulating material, e.g., an epoxy, covers the array of interconnect stripes and wires, forming a seal with the substrate and electrodes. The tips of the electrodes are exposed at at least one edge of the substrate. The tips of the electrodes exposed at the substrate edge are the working surface of the electrodes, i.e., the microband electrodes.

In another preferred embodiment, the substrate is annular, i.e., ring-shaped. The subtrate can be, for example, a rubber washer or a glass disk with an aperture bored through the middle. The aperture can be bored through the middle of the disk either before or after deposition of the electrode material. A plurality of deposits of electrically conductive material (electrodes), are positioned on at least one face of the annulus extending to the aperture in the center. In either case, the tips of the electrodes lie in the inner edge, i.e., along the circumference of the aperture in the center of the disk/annulus. This embodiment of the sensor, the annular sensor, can be integrated into a device for performing electrochemical measurements on a stream of fluid flowing through the aperture. For example, the annular sensor can be used in fluid connection with fluid channels flowing into and away from the annular sensor. Other types of analysis or treatment may be performed on the fluid sample upstream and/or downstream of the annular sensor. Electrodes can be deposited on both faces of the annulus.

In another embodiment, termed herein the channel embodiment, the exposed tips of the electrodes lie at the edge of a fluid channel, particularly a microchannel which affords laminar flow. In this microband electrode channel sensor, as in the annular sensor, electrochemical measurements can be performed as a sample flows through a device or intergrated systems of channels and devices.

In each of the embodiments mentioned above, the sensors can be stacked forming a multi-layered sensor comprising two or more sensors. Preferably a plurality of electrodes made of one type of electrically conductive material are on each sensor and the sensors composing the multi-layered sensor contain electrodes of various electrically conductive materials. The electrodes on one sensor may detect analytes with a certain redox potential, while the electrodes on the sensors above or below detect analytes with different redox potentials. A layer of insulating material separates the electrode layers. By stacking sensors with electrodes made of different conductive materials, a multi-layered sensor with a very broad detection range is provided.

DETAILED DESCRIPTION OF THE INVENTION

Figure 1A:
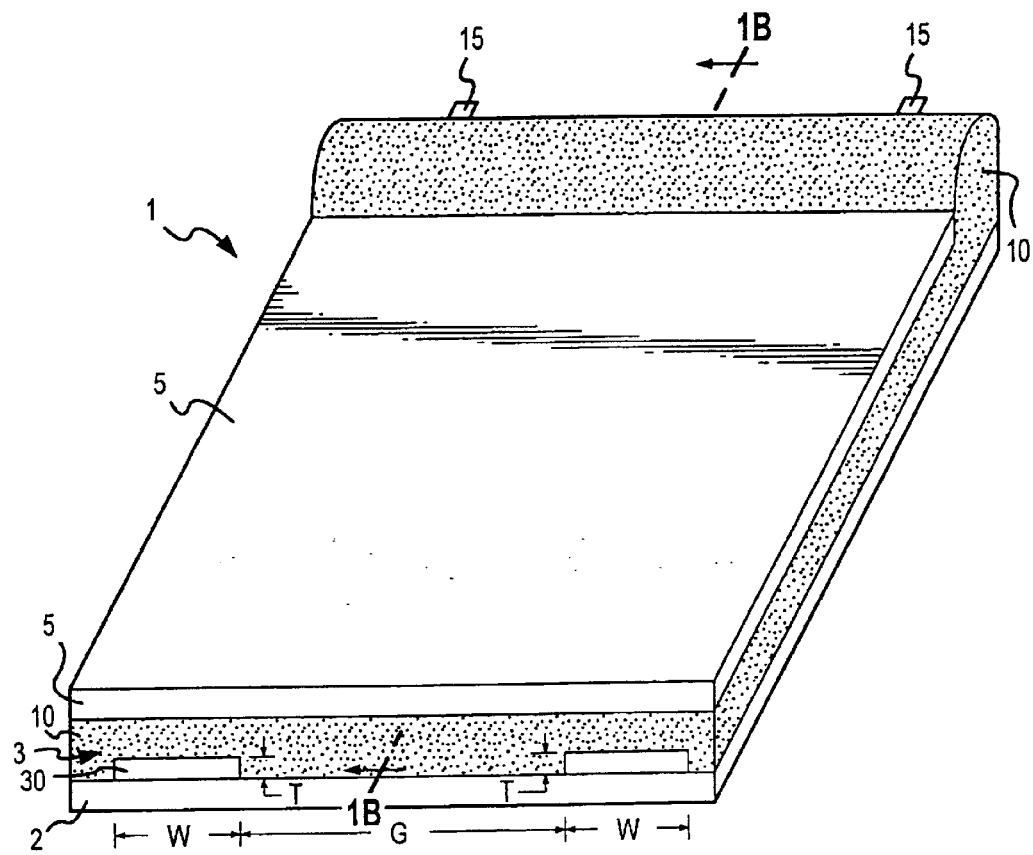
FIG. 1A is a perspective view of a planar sensor.

FIG. 1A is a perspective view of a planar embodiment of sensor 1. Shown are planar substrate 2 and microband electrodes 30 which are exposed at edge 3 of sensor 1. Electrodes extend from edge 3 to a bonding pad (not shown in FIG. 1A) at the other end of the sensor. Insulating material 10, e.g., an epoxy, is spread over the electrodes and forms a tight seal with substrate 2 and with the electrodes, the tips of which are the working microband electrodes 30. Cover plate 5, e.g., a microscope slide, provides a smooth surface and covers part of insulating material 10. Wires 15 provide electrical communication between microband electrodes 30 and peripheral devices such as potentiostats and voltmeters.

Microband electrodes 30 have a width (W) which ranges from about 1 micrometer to about 25 micrometers and a thickness (T) generally defined by the thickness of the photolithographically deposited material, which ranges from about 0.03 micrometers to about 5 micrometers. The thickness (T) is limited partly by what is practical, i.e., the thickness of a layer of photolithographically deposited material. Hence, the aspect ratio (W/T) ranges from about 1 to about 1000, preferably from above about 1 to about 800, and more preferably from about 1 to about 250. For example, a microband electrode with a width of 10 micrometers and a thickness of 0.01 micrometers has an aspect ratio of 10. The width can be made greater. than about 25 micrometers, but as the width becomes much greater than the thickness (assuming a gap sufficient to prevent diffusion layer overlap), the equilibration time increases. A microband electrode with a width much greater than about 25 micrometers may require impractically long equilibration times. In general, the dimensions (width and thickness) of the microband electrode are preferably substantially smaller than the characteristic diffusion length of the analyte of interest.

Figure 1B:
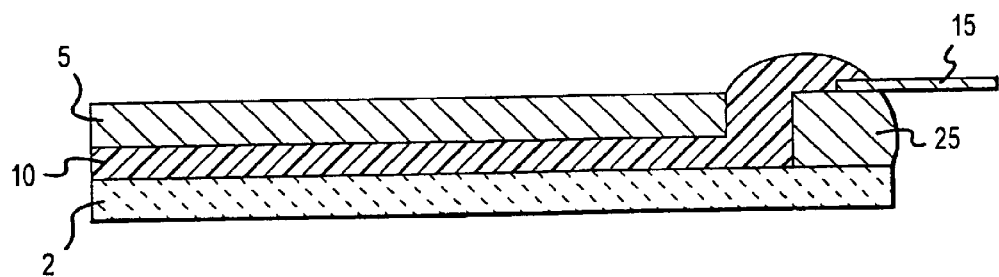
FIG. 1B is a side view of the planar sensor of FIG. 1A.

FIG. 1B is a side view of the sensor of FIG. 1A. Elements already discussed herein are indicated with the same numerals. Bonding pad 25 provides electrical connection between each electrode and peripheral devices.

Planar substrate 2 is preferably rigid and substantially chemically inert. Glass, quartz, sapphire, alumina or other ceramics, oxide coated silicon, or plastics such as polycarbonate or polystryene are preferred substrate materials. Substrate 2 is typically about 1 centimeter by about 2–3 centimeters, although the dimensions are chosen according to what is practical and convenient. Hence, the minimum dimension could be as small as a few millimeters and the maximum dimension is theoretically unlimited.

Figure 2A:
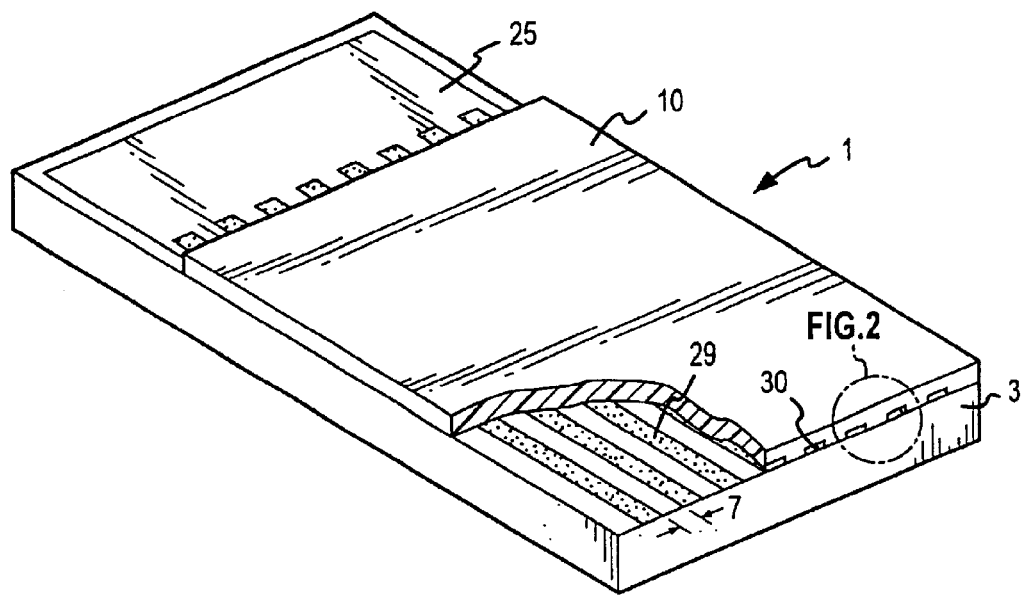
FIG. 2 is a perspective view of a planar sensor with a cut away section and an expanded view section.
Figure 2:
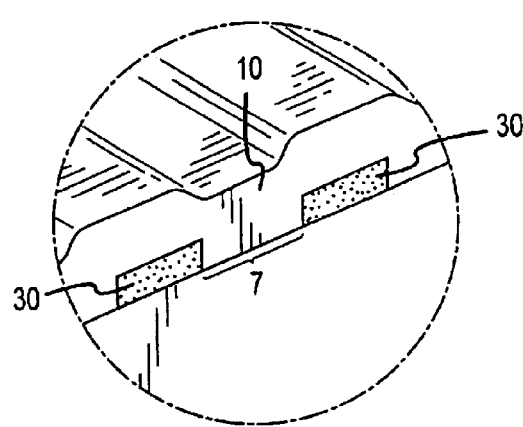

FIG. 2 is a perspective view of a planar embodiment of sensor 1 with a cut away section and an expanded view section and wherein the insulating material 10 is a thin film. Thin film insulators, e.g., silicon nitride, silicon carbide, silicon dioxide, and chemically deposited polymers, can be applied by evaporation, sputtering or chemical vapor deposition. Thin film insulators are, in general, preferable to epoxy insulators which are applied by manually spreading. No cover plate is needed if thin film insulator is used. Microband electrodes 30 are the exposed tips of the interconnect stripes (electrodes) 29. Gap 7 between adjacent microband electrodes 30 is larger than the diffusion layer (boundary layer) formed when the sensor is operating. Put another way, gap 7 is larger than a diffusion hemisphere diameter. Gap 7 provides that each microband electrode behaves independently and that there is no substantial interference or corruption of the measurement caused by overlapping diffusion layers. As discussed above, the size of the diffusion layer depends on many factors, including the length of time for a given measurement and the concentration of analyte in the sample, as will be understood by those in the art.

Figure 3:
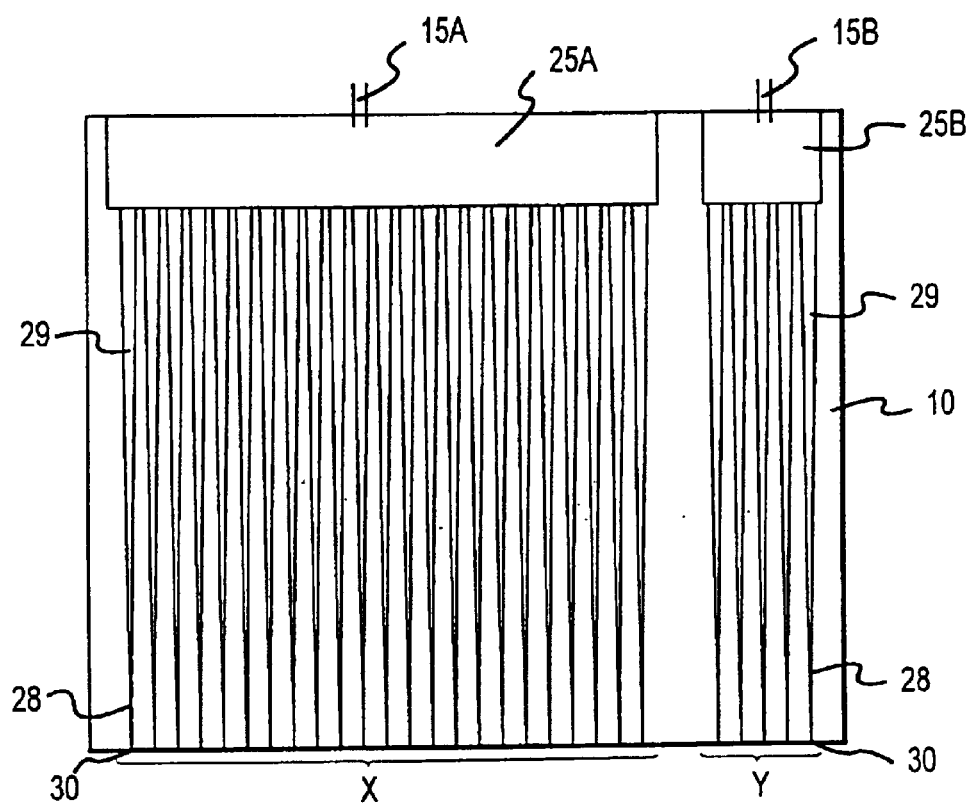
FIG. 3 is a plan view of a planar sensor.

FIG. 3 shows a cut away top view of a planar embodiment of sensor 1. In this example, sensor 1 contains 23 platinum electrodes (labeled X) and 5 gold electrodes (labeled Y). All 23 platinum electrodes are connected to a first bonding pad 25a which is connected to a first wire 15a, and all 5 gold electrodes are connected to a second bonding pad 25b which is connected to a second wire 15b. Each microband electrode 30 is the tip of an electrode base 28 which is connected to an interconnect stripe 29, all of which make up an electrode. The electrode base is often a few millimeters or more in length.

The electrodes can be formed by depositing a thin film of metal and patterning it using photolithography. The patterning can be accomplished, for example, by etch-back or lift-off techniques. The electrode material (conductive material) is preferably chosen from the platinide (noble) metals: ruthenium, rhodium, palladium, silver, rhenium, osmium, iridium, platinum, and gold; vitreous carbon or graphite; noble metal alloys; and various transition metals. As noted above, mercury electrodes can be used in this invention and are fabricated by plating mercury onto various metals, preferably iridium which does not dissolve in mercury (U.S. Pat. No. 5,378,343 by Kounaves and Kovacs). As will be understood by those in the art, each working electrode (conductive material) offers a specific scanning range for a given applied voltage, and choice of the electrode material is determined in part by the analyte(s) to be measured. The more electrodes of a given type which are in a set, the stronger the signal (and higher signal to noise ratio) will be from the added elctrode signals.

Etch-back and lift-off are well known microfabrication techniques, and will be only briefly explained.

The etch-back technique involves the patterned material, for example a metal, being deposited over the entire surface of the substrate by evaporation or sputtering. A photoresist layer is then applied over that and patterned by masked exposure to UV light. Where the photoresist layer is developed away to expose the metal, an etchant solution is used to remove deposited metal. The areas where the photoresist layer remain after development protects the metal film from the etchant. The photoresist layer is then stripped after the metal has been etched to form the desired pattern.

The lift-off technique involves application of a photoresist layer to the substrate, then patterning by masked UV exposure and subsequent development. The thin film to be patterned, e.g., a metal, is then deposited by evaporation or sputtering over top of the photoresist. Where the photoresist was developed away, the metal is deposited onto the substrate and bonds there. Where the metal is deposited onto the remaining photresist, the photoresist keeps the metal film from bonding to the substrate and allows these regions of the metal to be "lifted off" at the same time that the photoresist is stripped from the substrate.

After the metal film has been deposited and patterned, the entire surface is then coated with a layer of insulating material. Insulating material is a non-conductive material which provides a tight seal between the electrode material (interconnect stripes-and electrode bases) and the substrate. A seal which is not tight allows dead space between the insulating material and the electrodes, providing channels in which ions from the sample can become entrapped, yielding permanent fouling of the sensor. Preferably, the seal provides a leakage current of less than about 1 picoampere flowing between electrodes insulated from one another. Examples of insulating material include but are not limited to silicon dioxide, silicon nitride, silicon carbide, or low-temperature glass. Organic films such as photoresist resins, polyimides, or epoxies can also be used for the insulating coatings, but inorganic insulating coatings are preferable. The insulating coating is applied only from the bonding pad forward to the tips, so that it does not interfere with the electrodes' electrical contact to the bonding pad.

The patterning of the thin film electrode, e.g., metal, produces a series of electrodes which are one one edge of the substrate. The lateral spacing (pitch) of these stripes is designed to provide a gap between adjacent microband electrodes greater than the diameter of a diffusion hemisphere for the analyte(s) of interest, i.e. greater than the diffusion layer (boundary layer). Typically, this gap is greater than 25 micrometers, more typically greater than 50 micrometers. The exposed tip of each electrode constitutes the working surface of the microelectrode, and is rectangular (or square) in cross-section. The smaller dimension of the cross-section (T) is the thickness of the deposited film, preferably about 0.1 to about 0.2 micrometers. The larger dimension of the cross-section (W) is the width of the patterned electrode stripe at its tip, preferably about 2 to about 10 micrometers.

A plurality of electrodes is connected at the end opposite the working tips (microband electrodes) to a bonding pad for making an electrical connection.

The final step in the fabrication of the sensor is to polish the microband electrodes (the tips of the electrode stripes). Polishing can be done with alumina, carbide grit or other submicron abrasives. Preferably, the final grit size in polishing is about 0.03 micrometers to about 0.06 micrometers. For substrate materials which allow controlled cleaving, the microband electrodes can be prepared by cleaving off a small section of the end of the sensor to expose pristine electrode surfaces.

The poilishability of the microband electrode array sensor of this invention, i.e. the durability of the sensor upon multiple polishings, is one of its great advantages, allowing it to be re-used many, many times. It is preferable to choose a substrate, electrode material, and insulating material so that they offer the same wear rate to a given environment and upon polishing. The electrodes can be worn back the distance of the electrode base, e.g., by several millimeters, and still retain their precise cross-sectional geometry because the electrode base does not taper. This allows the sensor to operate for a much longer time than conventional surface disk microelectrodes. An example of a combination of substrate, electrode material, and insulating material of similar wear rates is a glass substrate, platinum electrodes, and silicon nitride insulating coating. The hardness of these three materials is very similar, so if the sensor were placed into an abrasive sample, each of these three components would erode at the same rate, keeping the cross-sectional geometry of the microband electrodes constant, as well as providing continuous polishing in-situ.

The planar embodiment of FIG. 2 can be used "as is," for a dip-probe in water sampling, or it can be embedded into a larger probe so that only the end or edge surface containing the microelectrode tips contacts the sample. This allows its use in locations on the side of a vessel, on the side of a plunge probe, or on the outside surface of some other device. The sensor of FIG. 2 can also included in a container or pipe.

The substrate can have electrodes formed on one or both of its faces. That is, thin film microelectrode metal and its insulating coating can be deposited on either or both the top and bottom faces of the substrate. In this case microband electrodes lie along the top and bottom portions of the substrate edge.

A solid-state reference electrode, such as an Ag/AgCl electrode, can be deposited onto either face of the substrate: This is optional, as a separate reference electrode can be contacted with the sample independently of the sensor of the present invention.

An auxiliary electrode can be implemented as one of the sets of electrodes (for example the set of 5 electrodes in FIG. 3) in the array and can be deposited onto either face of the substrate. It is preferable to include an auxiliary electrode when analyzing samples of low conductivity. For low conductivity samples, the auxiliary electrode can be useful for minimizing solution resistance errors. However, because the voltage drop across a sample solution to a microband electrode is small, there is generally no need to correct measurements with an auxiliary electrode.

The sensors of this invention can be stacked to form a multi-layer microband electrode sensor, with no theoretical maximum limit to the number of sensors stacked together. This allows multiple electrode materials (with different voltage scanning ranges and different analyte responses) to be integrated into the same multi-layer sensor, thereby increasing the scanning range and sensing dimensionality (because of different surface reactivities/responses) of the multi-layer sensor.

Figure 4A:
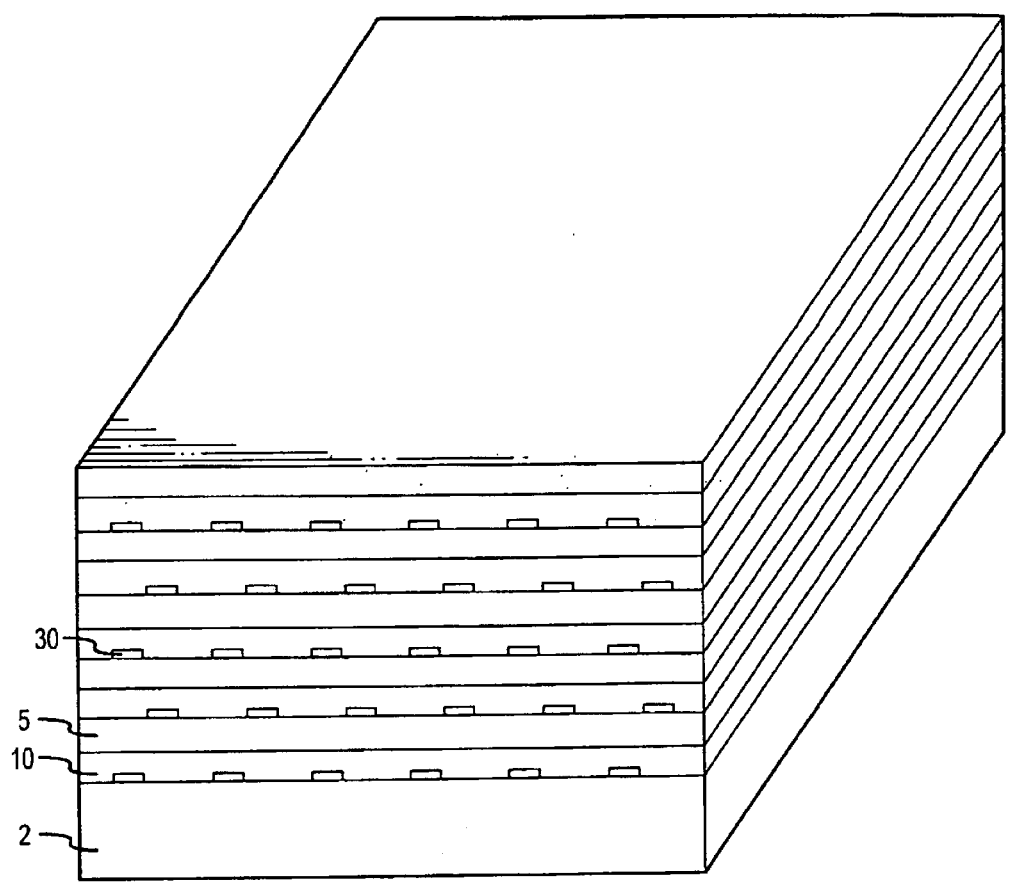
FIG. 4A is a perspective view of a stacked multi-layer planar sensor with epoxy as insulting material.

FIG. 4A shows a multi-layer microband electrode sensor with epoxy as the insulating material 10. A cover plate 5 is layered between each individual sensor, to create a smooth surface above the epoxy which is manually spread.

Figure 4B:
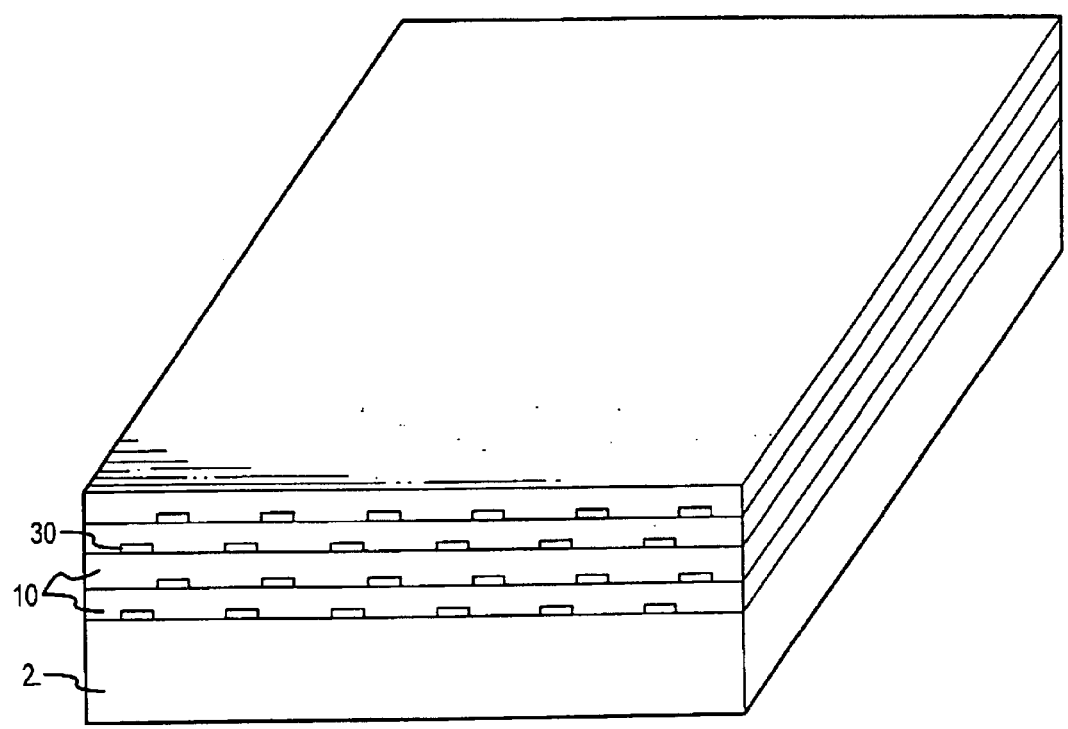
FIG. 4B is a perspective view of a stacked multi-layer planar sensor with thin film deposited as insulting material.

FIG. 4B shows a multi-layer microband electrode sensor with thin film deposited layer of insulating material 10. No cover plate is needed in this embodiment. Again, the thin film insulation can be applied by evaporation, sputtering, and chemical vapor deposition. The embodiment with thin film as insulating material (shown in FIG. 4B) is batch-process-capable (easily manufactured) and thus is preferable to the embodiment with epoxy as insulating material (shown in FIG. 4A).

The sensors and methods of this invention are useful in detecting the presence of and measuring the concentration of analytes in sample. The sample is a fluid, including ionized gases such as plasma, and preferably is a liquid. The present sensor and methods are useful in analyzing in samples which have a large volume (no maximum limit) to samples with very small volumes, e.g., in the milliliter range for the planar embodiment, and in the microliter range for the annular and channel embodiments wherein the microband electrodes lie in an edge of the sensor in fluid connection with microchannels.

Analytes which can be detected and measured are electroactive species, i.e., species which are capable of being oxidized and/or reduced. The analytes can be organic or inorganic, electrically neutral or ionic. Examples of analytes include but are not limited to metals and metal ions, e.g., titanium, chromium, manganese, iron, cobalt, nickel, copper, zinc, rubidium, lead, and iridium; quinones such as benzophenone; phenyl diamines; proteins, e.g., myoglobin and hemoglobin; dithiothreitol; and metal complexes with organic ligands such as iron-phenanthroline and ferricyanide/ferrocyanide. Other analytes are radionuclides such as uranium and plutonium, sulfites, phosphates, sulfides, flavins, purine derivatives and pyrimidine derivatives, thiosulfates, nitrates, nitrites, pharmaceutical compounds like aldosterone, catechols like resorcinol, phenols like p-methoxyphenol, aldyhydes, organic acids like ascorbic and maleic acid, and biological molecules like enzymes.

Figure 5A:
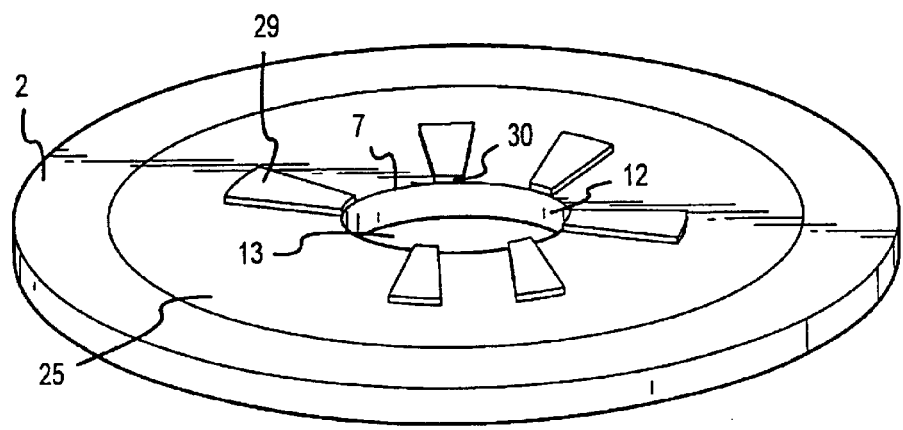
FIG. 5A is a cut away view of an annular sensor.

FIG. 5A shows a cut away view of the annular embodiment of the present sensor. The tips of electrodes 29 are microband electrodes 30 which lie on the inner edge 12 of the annulus. The inner edge 12 can be formed by boring an aperture 13 in the center of substrate 2.

Figure 5B:
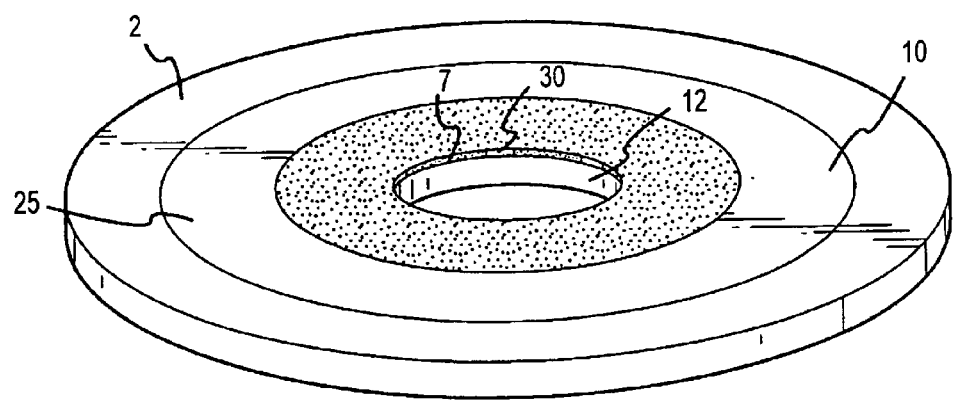
FIG. 5B is a perspective view of an annular sensor.

FIG. 5B is a perspective view of the sensor of FIG. 5A, the difference between the two figures being that 5B shows the insulating layer coating the top of electrodes 29 and filling the spaces between the elelctrodes. Microband electrodes 30 lie in inner edge 12 of the annular sensor.

The same fabrication steps as above are used in this embodiment, with the only difference being that the stripes of electrodes now overlap an aperture in the substrate. Preferably the aperture is circular, although apertures of different cross-sections, e.g., rectangular, can be used. This produces an array of microband electrodes which are spaced around the internal periphery/inner edge of an annulus. The aperture can be drilled or micromachined into the substrate before or after the electrode material and insulating coating are deposited. The diameter of the aperture and the number of electrodes is designed so that the distance between two adjacent microband electrodes is greater than the diameter of the a diffusion hemisphere for the analyte under investigation, i.e. so that the diffusion layers do not overlap.

As noted above, the annular sensor can be integrated into a flow-through system for samples to be flowing into the sensor from a channel in fluid connection with the sensor, i.e., the sample flows through the aperture. The annular sensors can also be stacked together to introduce more microband electrodes into the same fluid channel system and allow contact of a sample flowing through the channel system to contact a greater number of microband electrode types, each with its own scanning/detection range. The annular sensors resemble mechanical washers, and can be used in much the same way, e.g., as a gasket inside part of a all tubing or pipe fitting. The tubing or pipe fittings should be made of electrically insulating materials to avoid shorting out the microband electrode arrays. Compression fitting housings which insert one or more annular sensors into a small-bore tubing connector offer many applications in analytical chemistry, including end-point detectors for capillary electrophoresis, high-perfomance liquid chromatography, or as driving electrodes for electrophoresis or dielectrophoresis.

Figure 6A:
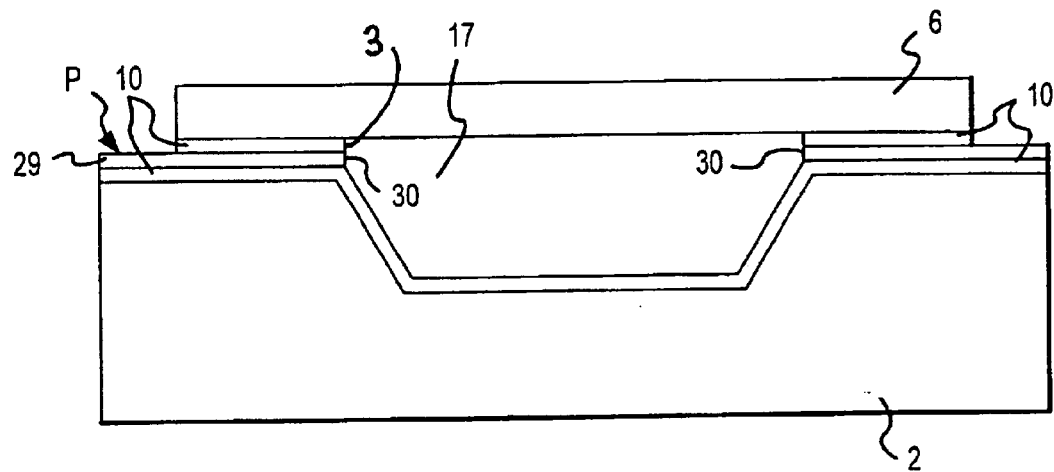
FIG. 6A is a cross-section of a channel sensor.

FIG. 6A is a cross-sectional view of the sensor in a channel embodiment. Microband electrodes 30 line the top edge of flow channel 17 so that analytes in the fluid sample flowing therethrough contact microband electrodes 30, producing an electrochemical signal. Cover plate 6 seals the flow channel. Electrical connection to electrodes 29 is made at point P.

Figure 6B:
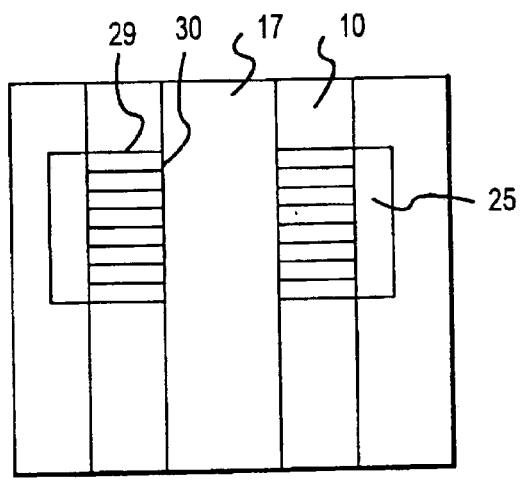
FIG. 6B is a plan view of a channel sensor.
Figure 7:
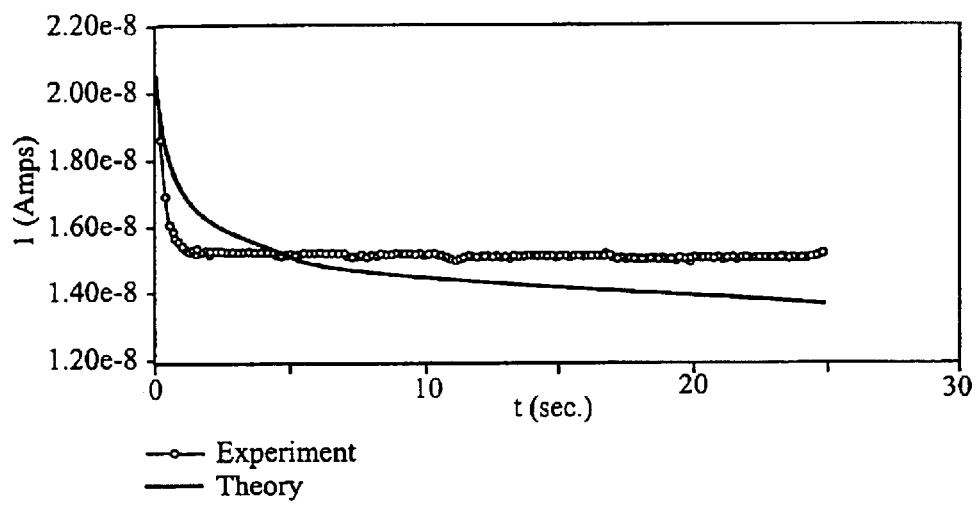
FIG. 7 is a chronoamperometric graph of experimental data from 10 Au band electrodes and the theoretic values.
Figure 8:
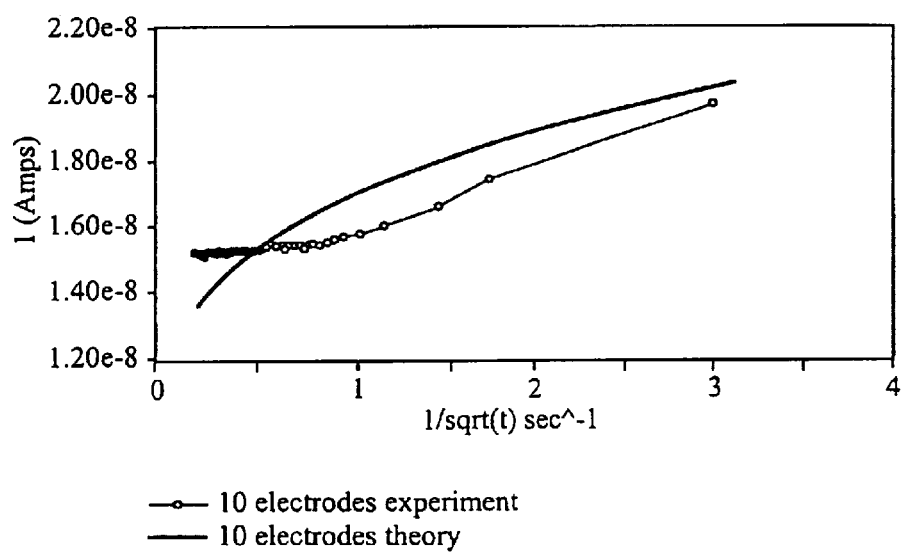
FIG. 8 is a chronoamperometric graph of experimental data from 10 Au band electrodes and the theoretic values.
Figure 9:
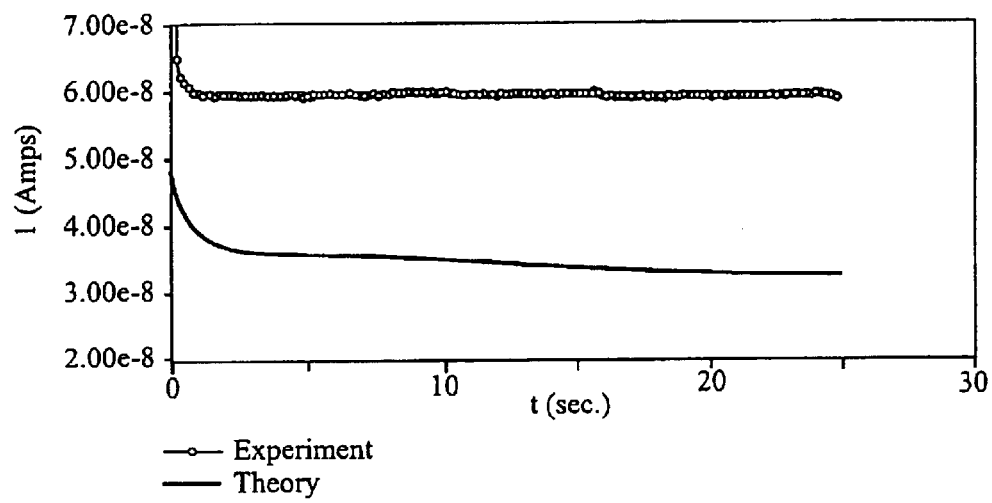
FIG. 9 is a chronoamperometric graph of experimental data from 24 Au band electrodes and the theoretic values.

FIG. 6B is a plan view of the sensor of FIG. 6A. Bonding pad 25 is connected to electrodes 29.

The channel embodiment of FIGS. 6A and 6B can be stacked to form a multi-layer sensor, i.e., a channel with several stacked layers of microband electrode arrays.

The channel embodiment of the present sensor can be combined with any type of flow-through analytical device. Channels etched in fused silicon wafers (quartz) are described in D. Sobek, S. D. Senturia, and M. L. Gray, *Proc. Solid State Sensors and Actuators Workshop*, Hilton Head, S.C., Jun. 13–16, 1994, pp. 260–263, IEEE. Channels etched into standard soda lime glass are described in A. T. Woolley and R. A. Mathies, *Proc. Natl. Acad. Sci.*, November 1994, 91:11348–11352. Channels etched in plastic are described in L. J. Gue'rin, M. Bossel, M. Demierre, S. Calmes, P. Renaud, *Proc. Internatl. Conf. on solid State Sensors and Actuators Workshop*, (Transducers'97) Chicago, Ill., Jun. 16–19, 1997, vol. 2 pp. 1419–1421, IEEE. Channels etched in silicon (inside out) are described in J. Chen and K. D. Wise, *Proc. Solid State Sensors and Actuators Workshop*, Hilton Head, S.C., Jun. 13–16, 1994, pp. 256–259, IEEE. U.S. patent application No. Ser. 08/625,808 filed Mar. 29, 1996 describes a laminar flow channel and is incorporated by reference in its entirety herein.

In the channel embodiment (as in the annular embodiment) the microband electrode array can be integrated into the fabrication of a microfluidic channel so that electrochemical analysis can be performed directly on the analyte within the channel without the need for withdrawing a sample. Preferably the microband electrodes are substantially flush with the substrate and insulating coating surfaces, thus they do not introduce any dead volumes or turbulence into the laminar flow system. Another advantage of intergating the present microband electrodes into microfluid channels is that electrode fouling can be inhibited or prevented. For example, if the present microband electrodes line the edge of one side of the laminar flow channel, the sample can be introduced from the other side of the channel and only small analytes diffuse across the channel to the side containing the microband electrodes. Large molecules remain on the side of the channel they were introduced to and do not cross the channel and therefore do not contact the microband electrodes. Hence, fouling of electrodes is minimized. Additionally, because a solution of buffer or the like can be maintained in continuous flow through the channel, the microband electrodes are continuously being washed, thereby additionally inhibiting fouling of electrodes.

The microband electrode arrays of the channel embodiment are fabricated by adding some additional steps to the existing fabrication sequence for a microfluid channel. One fabrication process sequence is to deposit the patterned electrode material, e.g., metal, and the insulating coating layer before etching the channel. By aligning the channel pattern to overlap the tips of the interconnect stripes (electrodes), etching the channel into the substrate exposes the ends of the stripes, producing the same microband geometry as in the other embodiments. Sealing the channel with a cover plate encloses the microband electrode array within the channel with access to the electrical bonding pad just beyond the extent of the cover plate.

The microband electrodes of this invention allow electrochemical analysis of samples without solution deoxygenation and without added supporting electrolyte. Dissolved oxygen reacts (electron transfer at the electrode) in a quasi-reversible to reversible rate and if the scanning rate is high enough, oxygen reduction is minimized. The small size and small currents usually do not introduce voltage drop errors from solution resistance.

The sensors of this invention can be used in most electrochemical techniques. The following is a brief listing of some common electrochemical techniques for which the present sensor is useful.

The type of analyte to be detected and/or identified will affect the choice of electrochemical technique to be employed. For instance, anodic stripping voltammetry is employed when the redox-active analyte is a metal, while cathodic stripping voltammetry is used for detection of anions, such as chloride and bromide. These techniques include, but are not limited to, electrogravimetry; controlled-potential coulometry; controlled-current coulometry; voltammetry; anodic- and cathodic-stripping voltammetry; cyclic voltammetry; square wave voltammetry; differential pulse voltammetry; adsorptive stripping voltammetry; potentiometric stripping analysis and amperometry. U.S. patent application No. 08/738,445 filed Oct. 25, 1996; Gary D. Christian, *Analytical Chemistry*, 4th ed., John Wiley and Sons, Inc. (1986)); A. Bard and L. R. Faulkner, *Electrochemical Methods: Fundamentals and Applications*. John Wiley, (1980); and P. t. Kissinger and W. Heineman, Eds., *Laboratory Techniques in Electroanalytical Chemistry*, 2nd ed., Marcell Dekker, (1990) describe many electrochemical techniques, and all of these references are incorporated in their entirety by reference herein.

There are several variations of voltammetric measurements, and most of these are due to changes in the type of potential waveform used (cyclic, staircase, AC, squarewave, pulse, and differential pulse voltammetry) and/or the addition of a preconcentration step (stripping voltammetry). Consequently, the choice of technique determines how many characteristics of the redox reaction can be measured and how well a given characteristic can be measured. The most versatile of the voltammetric measurements, in terms of the number of measurable characteristics is cyclic voltammetry.

Cyclic voltammetry consists of scanning linearly the potential of a stationary working electrode using a triangular potential waveform. The resulting voltammogram provides information about both the oxidation and reduction reaction which includes the thermodynamics of the redox processes, the kinetics of heterogeneous electron transfer reactions, analyte identification and quantitation, and analyte diffusion coefficients. Variations on cyclic voltammetry involve a change in the waveform used to minimize the effects of non-faradaic currents in the measurement. The primary cause of these non-faradaic currents is a capacitance that is inherent in any electrochemical measurement system and is caused by the formation of a layer near the surface of the electrode that is devoid of analyte. This capacitance is in parallel with the solution resistance and causes a charging or discharging current anytime the potential is changed. The time constant of the charging current is a product of the solution resistance (R) and the diffusion layer capacitance (C), and therefore any sampling of the current should occur at a time after a change in potential that is greater than the RC time-constant.

Stripping voltammetry is an electrochemical technique that offers excellent sensitivity by the addition of a preconcentration step to a standard voltammetric measurement. This technique is limited to analytes with high electron transfer rates and to analytes whose redox reaction by-products are solids or liquids. Anodic stripping voltammetry is used primarily for the determination of cations (e.g. $Cu^{2+}$, $Hg^{2+}$, $As^{3+}$) while cathodic stripping voltammetry is used for anions ($Cl^-$, $Br^-$). In anodic stripping voltamnmetry, a deposition potential, usually 0.3 to 0.5 V more negative than the redox potential, is applied to the working electrode for a sufficient time to allow for the analyte(s) to plate onto the sensing area, a period of time typically ranging from about 30 sec. to about 30 min. Those skilled in the art will appreciate how to determine the amount of time necessary for this pre-concentration (plating) step. During this time, ions are reduced at the electrode surface to form a solid or liquid. The amount of material plated onto the electrode surface is a function of both the deposition time and potential. After preconcentration, the potential is scanned in a positive direction using any of the waveforms listed above and the current is recorded. A 1000-fold increase in sensitivity over standard voltammetry is obtained due to the preconcentration step. In cathodic stripping voltammetry, the applied potential is 0.3 to 0.5 V more positive than the redox potential and, following preconcentration, the voltage is scanned in a negative direction. Cathodic stripping analysis is useful for determining anions that form salts at the surface of the electrode. Therefore, silver is a good choice for the determination of $Br^-$ and $Cl^-$ because the by-product of the redox reaction is AgCl or AgBr.

Anodic stripping voltammetry is a standard method used in electrochemistry to measure the presence of unknown ions in solution. In this technique a negative voltage is applied to a working electrode, relative to a reference electrode in solution. The potential of the working electrode can be controlled relative to the reference electrode by adjusting the applied voltage between the working electrode and an auxiliary electrode. A potentiostat allows for the measurement of the potential diference between the working and reference electrodes with minimum loss due to solution resistance.

In anodic stripping voltamnmetry, redox-active analytes, such as metal cations, are electroplated onto the surface of an electrode and then electrically stripped off. The current which flows during the stripping process is proportional to the analyte concentration, and the voltage at which the stripping occurs corresponds to the redox potential unique to the analyte. A negative voltage is applied long enough so that positive ions in solution are reduced and concentrated at the surface of the electrode. Following the reduction step, the voltage is scanned/incremented in positive steps at specified time intervals, while simultaneously measuring the current flow in the electrode. A current peak occurs at the Nernst potential, which corresponds to the oxidation of ions back into solution. Based on the potentials at which the current peaks occur, it is possible to identify the different ions in solution. The height of the current peak is linearly proportional to the concentration of the ions.

Cathodic-stripping voltammetry is analogous to anodic-stripping voltammetry, the difference being that initially a positive voltage is applied to the working electrode, leading to oxidation of the analyte, whereby plating of the oxidized analyte occurs, followed by scanning the voltage in a negative direction to reduce the species off the sensor.

Amperometry involves voltammetric recordings at a fixed potential. This allows for detection of changes in currents as a function of concentration of redox-active species. Amperometry can be used to perform titrations and is very similar to voltammetry.

This invention will be more fully understood by reference to the following examples and construction methods, which are intended to be representative of the invention, but are in no way limiting. The invention is limited only by the claims appended hereto

EXAMPLES

Example 1

Photolithography

The smallest band width dimension was 2 $\mu$m and was incrementally increased in 8 $\mu$m intervals to a final width of 100 $\mu$m. The finger length for each increment was 5 mm. The reason for this design was two-fold. First, the design assured that a band width of less than 25 $\mu$m was possible. Since the films were designed to be 0.1 to 0.2 $\mu$m thick and several centimeters long, incrementally widening the band width would increase the cross-sectional area of the electrodes and reduce electrical resistance. All thin films were deposited on glass microscope slides using either thermal evaporation (Ag, Au) or electron beam (e-beam) evaporation (Pt).

A useful photolithograpic procedure is given in the steps below:

1. Clean, degrease and bake-out glass slides.
2. Allow glass to cool and apply Shipley Microposit 1400–27 positive photoresist to the glass substrate.
3. Spin photoresist onto glass substrate at 2500 rpm for 30 seconds.
4. Using a razor blade, remove the edge bead from around the edges of the glass substrate.
5. Pre-bake photoresist for 2 minutes at 100° C. in a convection oven.
6. Allow photoresist to cool and place sample in the contact aligner (Oriel Contact Aligner) with photomask in place. Align sample under the photomask. Once aligned, use the vacuum supply to make sure glass substrate is in contact with the mask.
7. Expose the photoresist through the mask using a UV light source set at 340 Watts for 10 seconds.
8. Develop the photoresist using Shipley 354 Developer for 10 seconds.
9. Rinse immediately in DI water and blow dry with a nitrogen gun.
10. Post-bake for 3 minutes at 100° C. (This step was not performed for Pt band electrodes.)

Inspection of the glass substrate under a microscope revealed clean, sharp features. The minimum feature size obtained was 10 $\mu$m and was well within the criteria for microelectrode behavior. The reason that a post-bake is not required in the fabrication of Pt electrodes is due to the heat generated in the e-bean evaporator during the deposition of Pt. This generated heat serves as an in-situ post-bake step.

Thin-Film Evaporation

Evaporation of thin films of Ag and Au were done using a CVC thermal evaporator with film thickness monitored by a Inficon XFS-3 quartz crystal monitor. To obtain a thickness of 0.2 $\mu$m, 1.2 grams of metal was placed into a tungsten filament in the growth chamber. After the samples were in place, the chamber was evacuated to a final pressure of between $3 \times 10^{-6}$ Torr and $5 \times 10^{-6}$ Torr. Deposition of a 0.1 μm film required no more than fifteen minutes once an adequate chamber pressure was reached. Evaporation of thin films of Pt were done using a NRC-3177 electron beam evaporator. Film thicknesses for Pt films were also monitored using a quartz crystal monitor. Platinum films were deposited at a pressure of $6 \times 10^{-6}$ Torr. A 0.1 μm film required no more than twenty minutes. After depositing the thin film, the remaining photoresist was removed using acetone and the samples were then rinsed in DI water and blown dry with a nitrogen gun.

The deposition of platinum proved to be much easier due to the excellent adhesive properties of Pt on glass. A summary of the fabricated band electrodes is given in Table 1. This table includes the critical dimensions of the electrodes and the typical measured resistances from bonding pad to electrode tip.

TABLE 1

Critical Dimensions and Electrical Resistances of Microband Electrodes

| Band Electrodes | Band Thickness (μm) | Band Width (μm) | Typical Measured Resistance (Ω) |
|---|---|---|---|
| Au | 0.1800 | 10.0 | 6.88 |
| Ag | 0.0600 | 10.0 | 9.03 |
| Pt | 0.1172 | 10.0 | 7.11 |

Chronoamperometric and Cyclic Voltammograms of Au and Pt Band Electrodes

Figure 10:
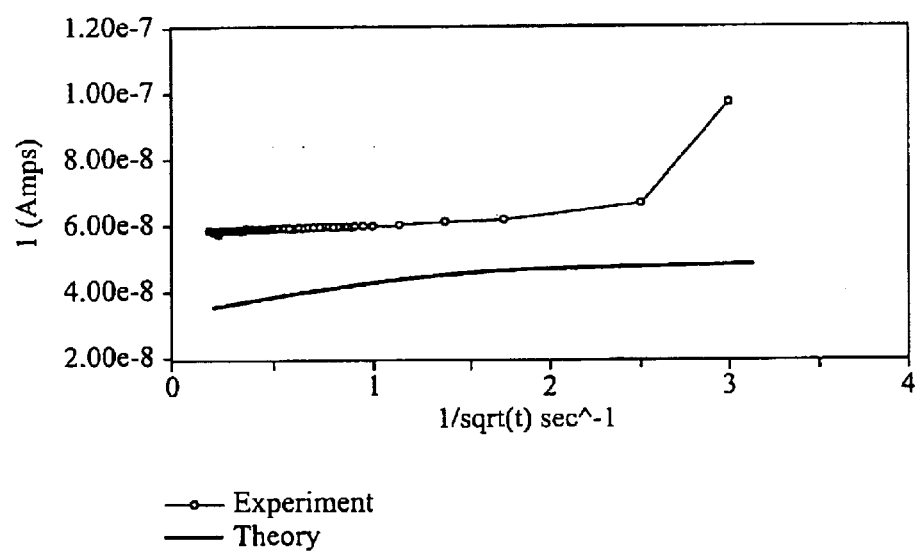
FIG. 10 is a chronoamperometric graph of experimental data from 24 Au band electrodes and the theoretic values.
Figure 11:
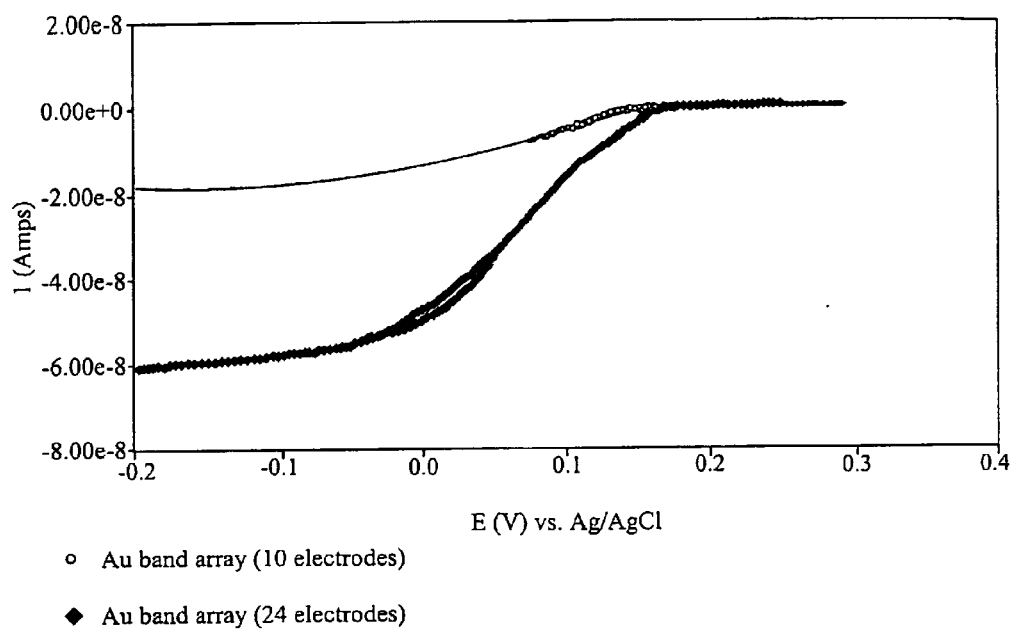
FIG. 11 is a steady-state cyclic voltammogram for Au band electrodes.
Figure 12:
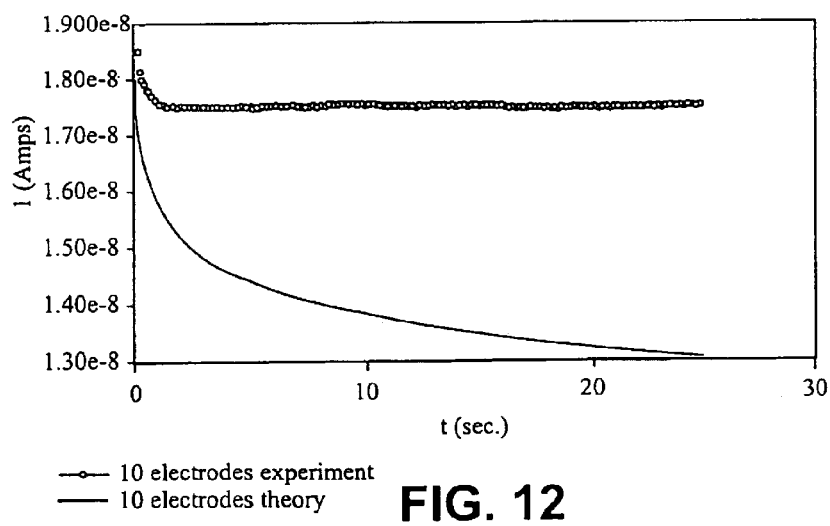
FIG. 12 is a steady-state cyclic voltammogram for Pt band electrodes.
Figure 13:
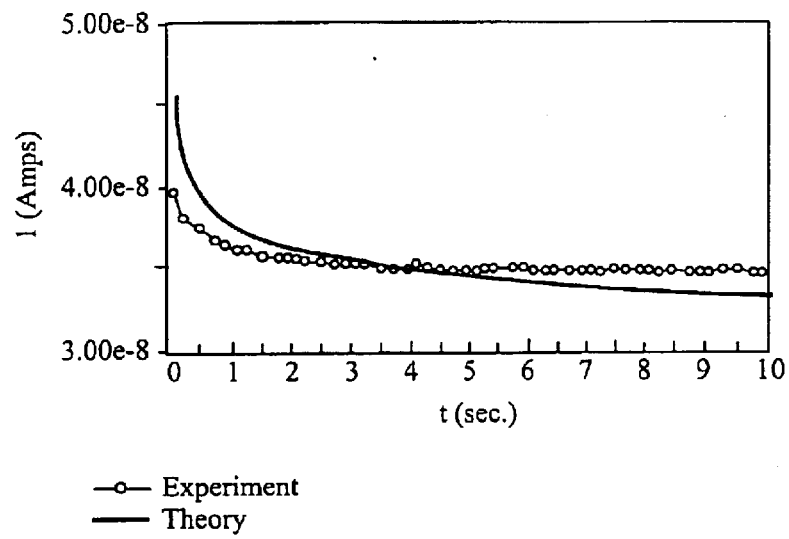
FIG. 13 is a chronoamperometric graph of experimental data from 24 Pt band electrodes and the theoretic values.
Figure 14:
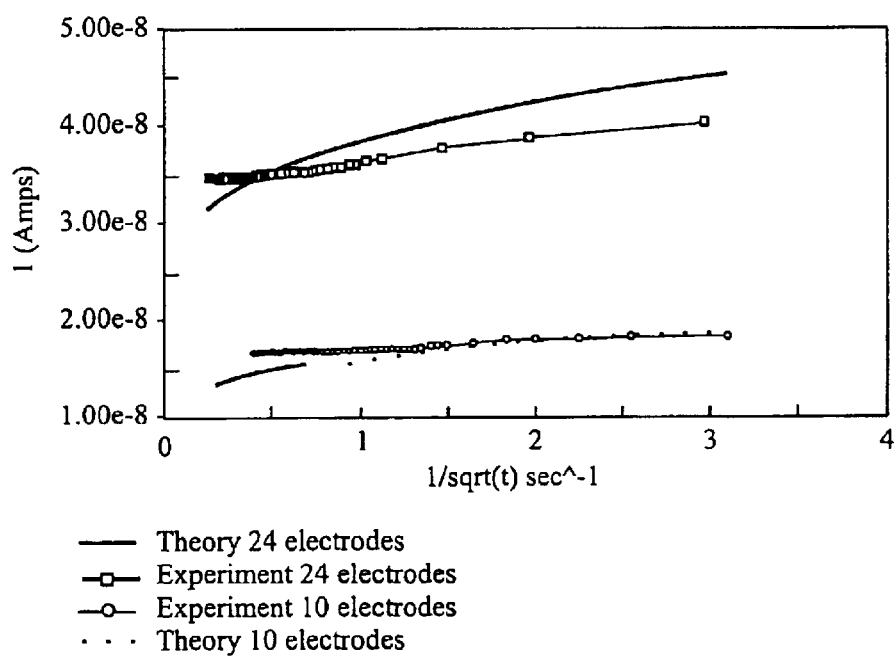
FIG. 14 is a chronoamperometric graph of experimental data from 24 Pt band electrodes and the theoretic values.
Figure 15:
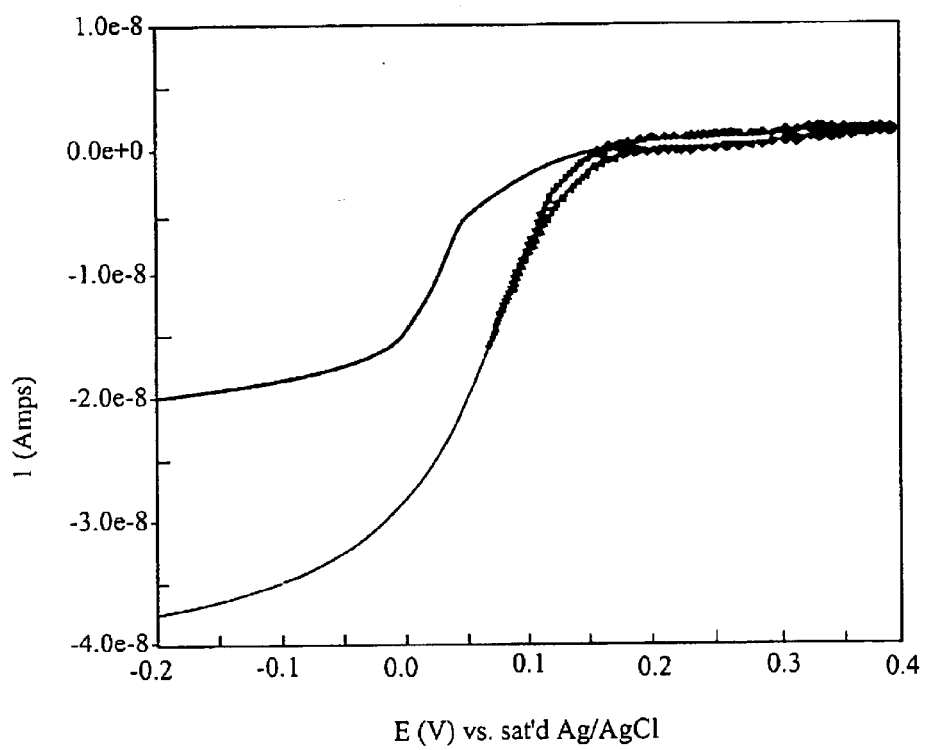
FIG. 15 is a steady-state cyclic voltammogram for 10 and 24 Pt band electrodes.

Chronoamperometric and cyclic voltammograms were performed on the Au and Pt band electrodes in a 5 mM ferricyanide solution with a 1 M KCl supporting electrolyte. The data for the Au band electrodes is presented in FIGS. 7 through 11. A clear deviation from conventional band electrode theory is evident, in favor of a steady-state response. This cannot be attributed to band recession since this would involve a much lower limiting current than seen from these electrodes (Wightman R. M. and Wipf, D. O. *Electroanal. Chem.*, 1989, 15:267). The unusually high limiting current for the array of twenty-four Au band electrodes can be explained in terms of a less than ideal seal. This is indicated in FIG. 10 where the large deviation at 3 $sec^{-1/2}$ can be attributed to a large capacitive discharge. This behavior is typical when the seal between electrode and substrate is not ideal.

Example 2

Better behavior is observed with the Pt band arrays and this data is given in FIGS. 12 through 15. Clear indications of steady state behavior are present in the chronoamperometric data and the magnitude of the current appears to be proportional to the width of the bands and close to theoretical values indicating that band recession is not a problem.

The design of well spaced microband electrodes in which both band dimensions are within the microelectrode regime offer advantages over conventional band electrodes in terms of steady-state behavior. By fabricating well-spaced arrays, large measurable currents can be obtained and the electrode is more efficient terms of surface area utilization resulting in better signal to noise ratios and reduced capacitive effects due to the growth of the diffusion layer.

A summary of the properties of the microband electrodes fabricated in this invention versus microdisk electrodes is presented in Table 2. The efficiency of the microband electrode structures over the microdisk electrodes is immediately apparent by comparing the diffusion limited currents to the active surface areas and perimeters. A 25 μm diameter microdisk electrode has 17 times the surface area of twenty-four (10 μm×0.1172 μm) Pt band electrodes, yet the diffusion limited current for the band electrodes is approximately 1.5 times larger and the band electrodes

TABLE 2

Comparison of Electrodes Fabricated in This Study

| Electrode | Surface Area (μm)$^2$ | Perimeter or edge Width (μm) | θ | $i_L$ exp (nA) | $i_L$ theory (nA) | % diff. | Seal Quality |
|---|---|---|---|---|---|---|---|
| Disk-1 | | | | | | | |
| Au | 490.87 | 78.54 | 0.9999 | 26.2 | 19.01 | 37 | POOR |
| Pt | 490.87 | 78.54 | 0.9999 | 20.9 | 19.01 | 9 | FAIR |
| Ag | 490.87 | 78.54 | 0.9999 | 19.0 | 19.01 | 0 | NA |
| Disk-2 | | | | | | | |
| Pt | 490.87 | 78.54 | 0.9998 | 23.7 | 19.01 | 24 | GOOD |
| Disk-3 | | | | | | | |
| 10 Au | 4900.87 | 785.43 | 0.9998 | 193.0 | 90.01 | 2 | GOOD |
| 6 Pt | 2945.24 | 471.24 | 0.9998 | 150.7 | 111.41 | 35 | GOOD |
| 5 C | 192.42 | 109.96 | 0.9999 | 24.6 | 26.26 | 6 | POOR |
| BAND | | | | | | | |
| 10 Au | 18.00 | 100 | 0.9994 | 5.3 | NA | | GOOD |
| 24 Au | 43.20 | 240 | 0.9994 | 58.8 | NA | | GOOD |
| 10 Pt | 11.72 | 100 | 0.9994 | 17.4 | NA | | GOOD |
| 24 Pt | 28.13 | 240 | 0.9994 | 34.4 | NA | | GOOD |

**NA Not Available or Determinable exhibit comparable steady-state behavior. A comparison of the perimeter or edge width of the microdisk and microband electrodes indicates that most of the flux at a microdisk electrode does occur at the perimeter. The edge for twenty-four band electrodes is 3 times larger than a 25 μm diameter disk electrode, this accounts for the larger diffusion limited current at band electrodes when non-uniformities in polishing are taken into account. Since the signal-to-noise ratio is a function of the surface area, it is clear that the microband structures of this invention are ideal for electrochemical sensors.

Example 3

Figure 16:
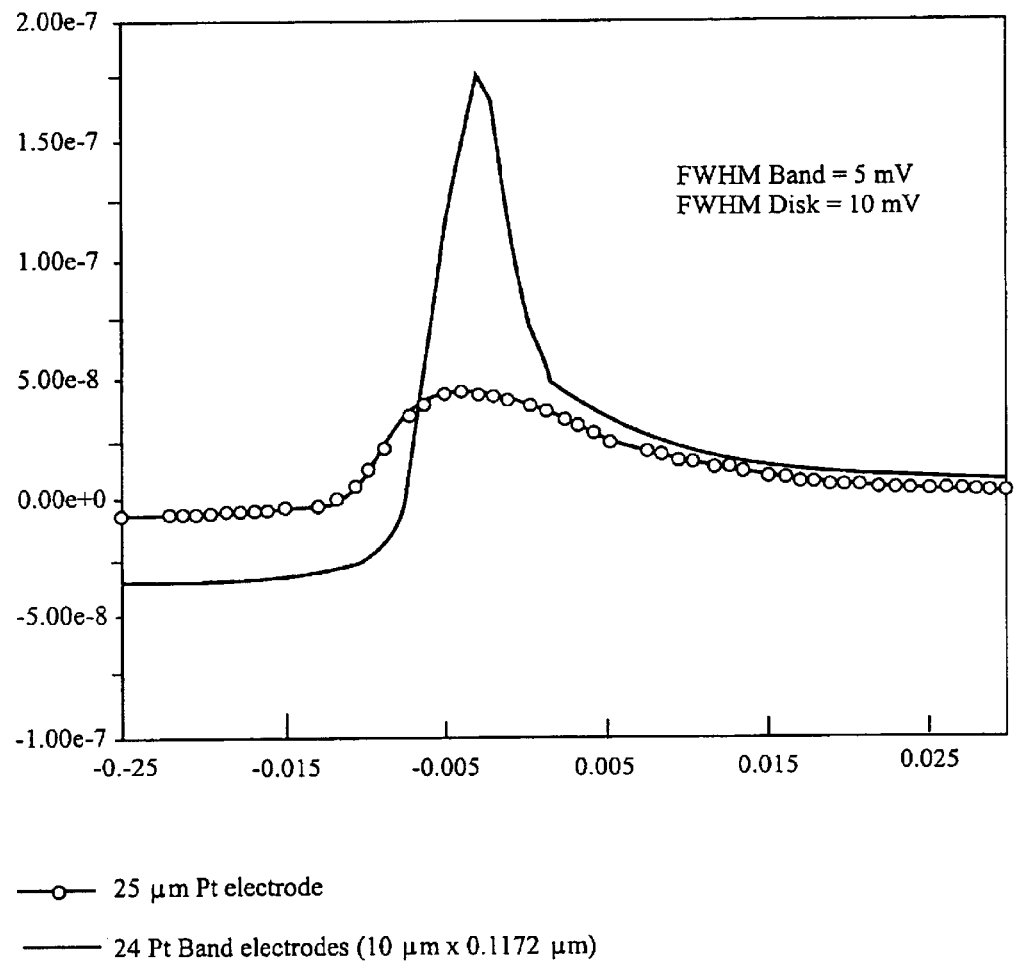
FIG. 16 is a steady-state cyclic voltammogram comparing Pt microdisk and Pt band electrodes.

A voltammetric measurement was made using 100 ppm Hg(II) solution in a 0.012 M HCl supporting electrolyte to compare the response of a 25 μm diameter microdisk Pt electrode and twenty-four (10 μm×0.1172 μm) Pt band electrodes. FIG. 16 shows that Pt microband electrodes provide a smaller peak width, higher peak current, and a better signal-to noise ratio than does a Pt microdisk.

Example 4

Simultaneous Determination of Cu(II) and Hg(II) at Microband Electrodes

Figure 17:
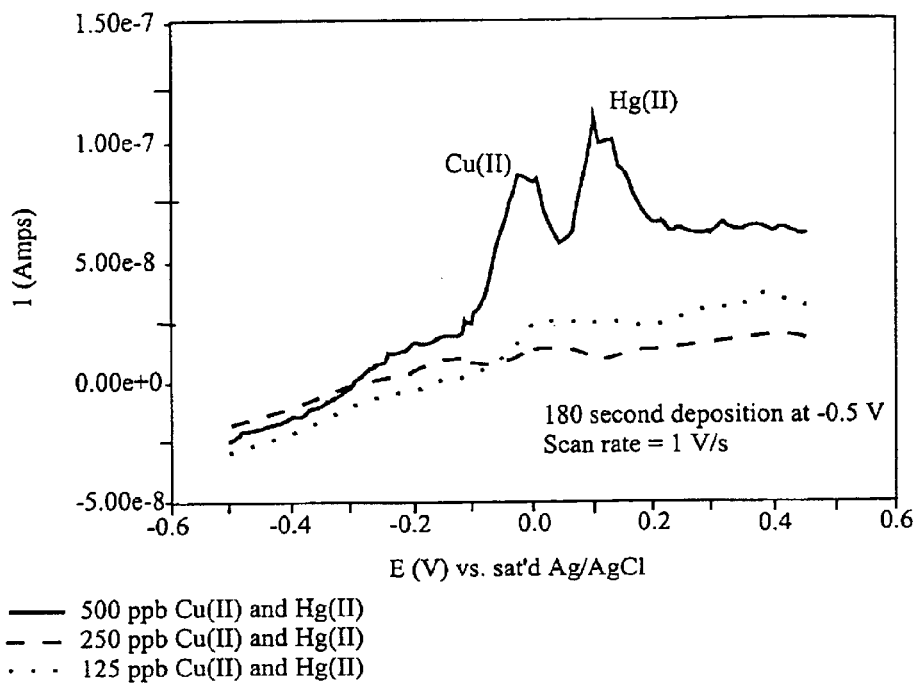
FIG. 17 ASSSV determination of Cu(II) and Hg(II) using an array of ten 25 micrometer Au microdisk electrodes.
Figure 18:
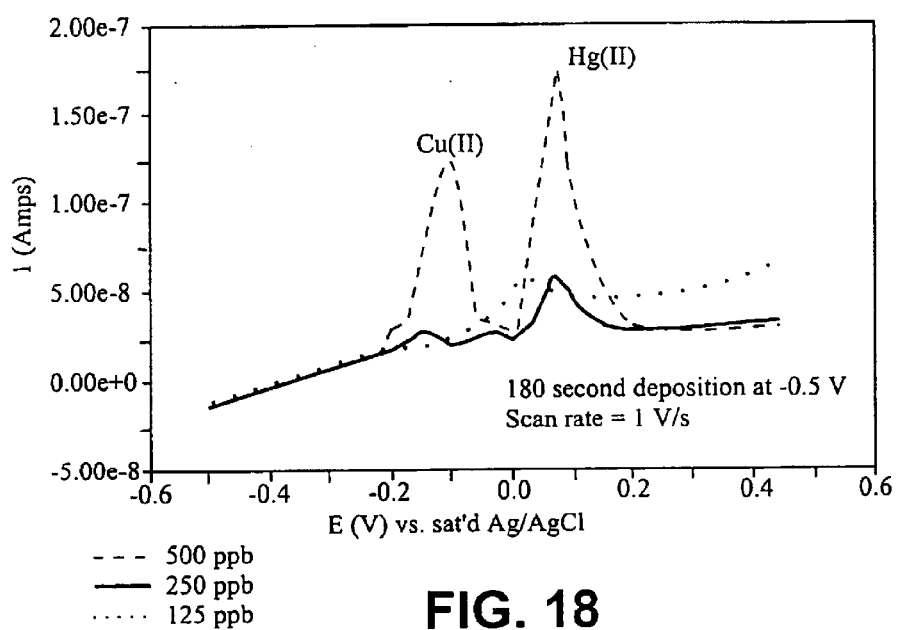
FIG. 18 ASSSV determination of Cu(II) and Hg(II) using an array of six 25 micrometer Au microdisk electrodes.
Figure 19:
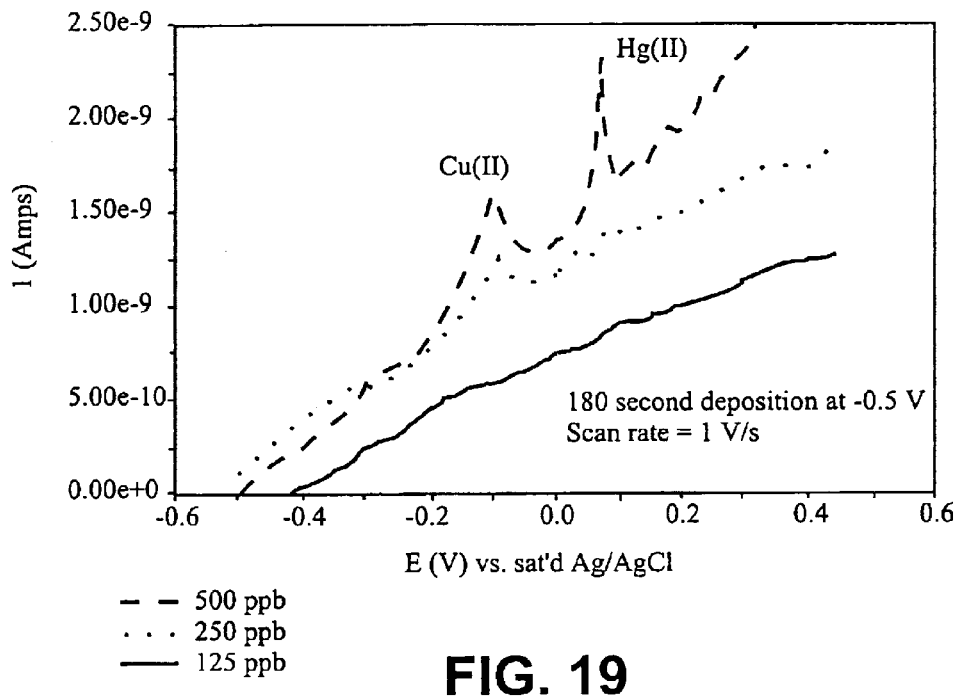
FIG. 19 ASSSV determination of Cu(II) and Hg(II) using an array of ten 7 micrometer carbon microdisk electrodes.

Due to the high mass transport rate constants associated with microband electrodes, it was decide to test the response of the Pt and Au band arrays in aqueous solutions containing trace amounts of Cu(II) and Hg(II) without any deliberately added supporting electrolyte and without solution deoxygenation. As an indication of the sensitivity of the band electrodes, similar measurements in the same solution were made using microdisk array electrodes as described in U.S. provisional application Ser. No. 60/030,319, which was filed on Nov. 1, 1996. For these measurements, background subtraction was not used so the true nature of the electrode responses could be observed. FIG. 17 shows the response of an array of ten 25 μm diameter Au microdisk electrodes. As can be seen from the figure, the maximum sensitivity obtained with a 180 second deposition was 500 ppb. Slightly better results were obtained with an array of six 25 μm diameter Pt microdisk electrodes. The maximum sensitivity for the Pt array was 250 ppb with a 180 second deposition time and is illustrated in FIG. 18. The same sensitivity was also obtained with an array of ten 7 μm diameter carbon microdisk electrodes. As illustrated in FIG. 19, the maximum response for the carbon array was also 250 ppb for a 180 second deposition time.

Figure 20:
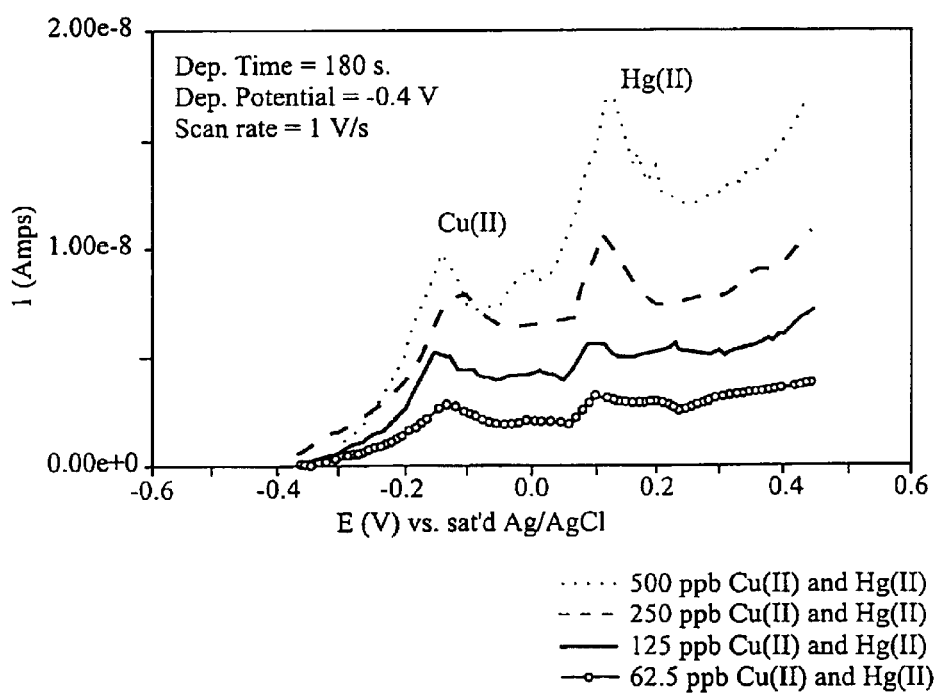
FIG. 20 ASSSV determination of Cu(II) and Hg(II) using an array of twenty-four Au microband electrodes.
Figure 21:
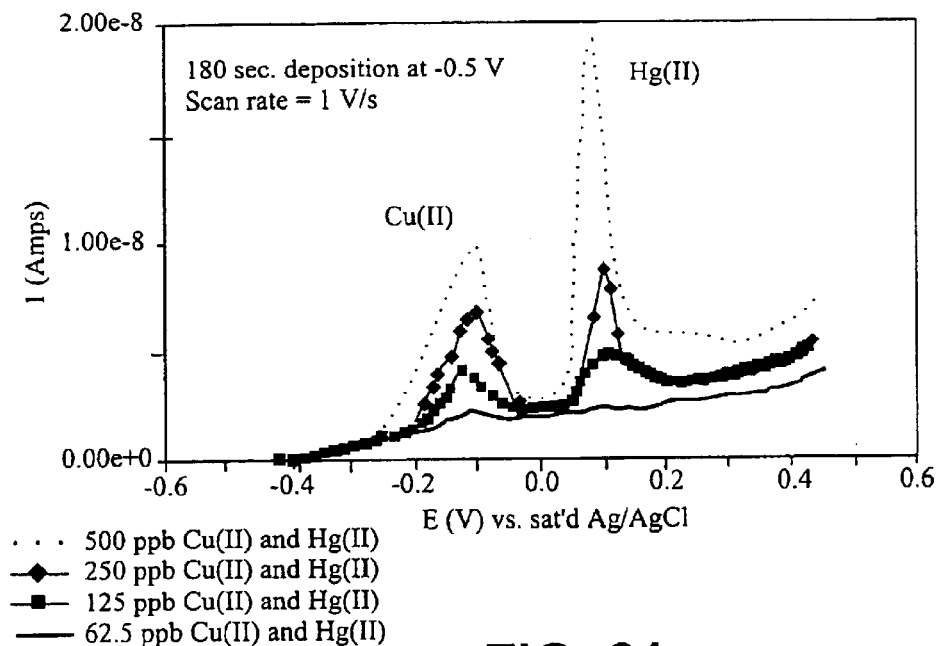
FIG. 21 ASSSV determination of Cu(II) and Hg(II) using an array of twenty-four Pt microband electrodes.
Figure 22:
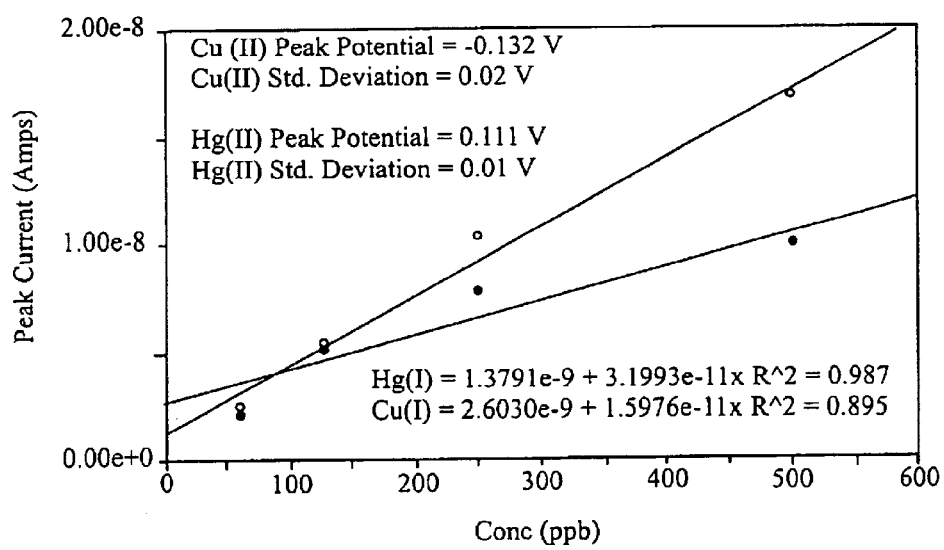
FIG. 22 Calibration curves for Cu and Hg at an array of twenty-four Au microband electrodes.
Figure 23:
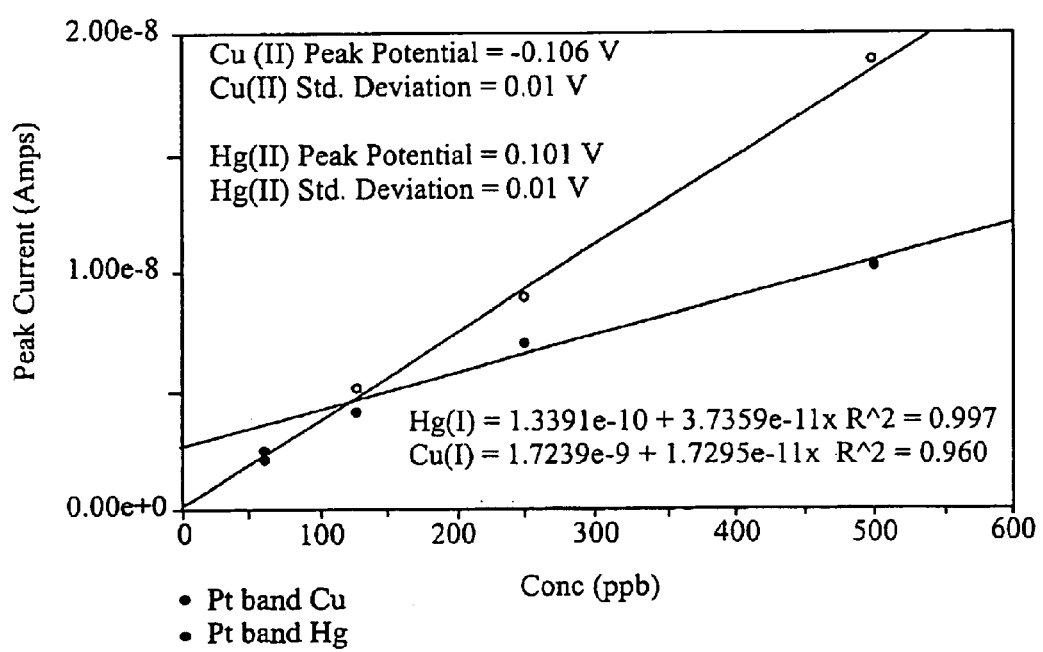
FIG. 23 Calibration curves for Cu and Hg at an array of twenty-four Pt microband electrodes.

The sensitivities for the Au and Pt microband electrodes were far superior to the microdisk arrays. For the same deposition time (180 seconds), the Pt and Au band arrays were four times as sensitive as the best microdisk arrays. FIGS. 20 and 21 show the responses of the Au and Pt band arrays, respectively. By comparing the two graphs, it can be seen that the Pt band array provides a better signal than the corresponding Au band array. This can be attributed to a better seal between the electrode and the epoxy for the Pt electrodes. Some noise in the signal may be coming from activity at the 20 angstrom Cr adhesion layer which is part of the Au band electrodes but it is more likely that a poor seal is to blame. This is apparent from the sloping nature of the stripping voltammograms for the Au band electrodes. Calibrations of peak currents vs. analyte concentrations are presented in FIGS. 22 and 23. For both the Au and Pt band arrays good linearity of the calibration curves is observed. For 300 second deposition times, detection limits of 10 ppb for both Cu and Hg are possible in solutions without a deliberately added supporting electrolyte and without solution deoxygenation.

Numerous embodiments besides those mentioned herein will be readily apparent to those skilled in the art and fall within the range and scope of this invention. All references cited in this specification are incorporated by reference herein in their entirety. The following examples illustrate the invention, but are in no way intended to limit the invention.

We claim:

1. A method of utilizing a microband electrode array sensor, said method comprising the steps of:
    (a) providing said microband electrode array sensor comprising:
        a substrate having a first edge;
        a layer of insulating material on top of said substrate, said layer of insulating material having a first edge, wherein said insulating material is chosen from the group consisting of silicon carbide, silicon nitride, and silicon dioxide;
        said first edge of said substrate and said first edge of said insulating material aligned to form a single edge;
        a plurality of microband electrodes between said substrate and said layer of insulating material, a surface of each of said microband electrodes exposed at said single edge wherein the exposed surface of each of said microband electrodes has a width less than about 25 micrometers and a thickness less than about 25 micrometers; and,
        a plurality of gaps of selected lengths, one gap positioned between each of two adjacent microband electrodes;
    (b) contacting said microband electrode array sensor with a sample suspected of containing an analyte; and
    (c) performing anodic stripping voltammetry, wherein the lengths of said gaps are each larger than the sum of the lengths of diffusion layers surrounding adjacent microband electrodes formed upon establishing steady state conditions at the surface of each of said microband electrodes, and wherein said microband electrode array sensor generates a steady state signal equal to the sum of the signals produced by each of said microband electrodes when operated independent of said microband electrode array sensor.

2. A method of utilizing a microband electrode array sensor, said method comprising the steps of:
    (a) providing said microband electrode array sensor comprising:
        a layer of insulating material having a first edge aligned with said first edge of said substrate; and
        a plurality of microband electrodes between said substrate and said layer of insulating material; said microband electrodes having a surface exposed at said first edges of said substrate and said insulating layer, said insulating material forming a plurality of gaps of selected lengths, wherein there is one gap positioned between each of two adjacent microband electrodes and, wherein the exposed surface of each of said microband electrodes has a width less than about 25 micrometers and a thickness less than about 25 micrometers;
    (b) contacting said microband electrode array sensor with a sample suspected of containing an analyte; and
    (c) applying a voltage to the microband electrodes of said microband electrode array sensor and scanning the voltage over a range such that said analyte should be oxidized or reduced at said microband electrodes wherein the lengths of said gaps are each larger than the sum of the lengths of diffusion layers surrounding adjacent microband electrodes formed upon establishing steady state conditions at the surface of each of said microband electrodes, and wherein said microband electrode army sensor generates a steady state signal equal to the sum of the signals produced by each of said microband electrodes when operated independent of said microband electrode array sensor.

3. The method of claim 2 wherein the voltage is scanned from a negative voltage to a positive voltage.

4. The method of claim 2 wherein said insulating material of said sensor is selected from the group consisting of silicon carbide, silicon nitride, and silicon dioxide.

5. The method of claim 2 wherein the exposed surface of each of said microband electrodes has a thickness of between about 0.03 and 5 micrometers.

6. The method of claim 2 wherein the exposed surface of each of said microband electrodes has a thickness of between about 0.1 to about 0.2 micrometers.

7. The method of claim 2 wherein the exposed surface of each of said microband electrodes has a width between 1 to 25 micrometers.

8. The method of claim 2 wherein said microband electrode array sensor further comprises an adhesion layer between said insulating layer and said microband electrodes.

9. The method of claim 8 wherein said adhesion layer comprises chromium.

10. The method of claim 2 wherein said substrate is planar.

11. The method of claim 2 wherein said sensor is integrated into a channel.

12. The method of claim 2 wherein the sample is contacted with a plurality of layers of microband electrode array sensors separated from each other by insulating material.

13. The method of claim 12 wherein in the multi-layer microband electrode array sensors each of said substrates is planar.

14. A method for performing electrochemical measurements on a sample suspected of containing an analyte, said method comprising the steps of:
- (a) providing a microband electrode array sensor that is integrated into a channel, said microband electrode array sensor comprising:
  - a substrate having a first edge;
  - a layer of insulating material having a first edge aligned with said first edge of said substrate; and
  - a plurality of microband electrodes between said substrate and said layer of insulating material; said microband electrodes having a surface exposed at said first edges of said substrate and said insulating layer, said insulating material forming a plurality of gaps of selected lengths, wherein there is one gap positioned between each of two adjacent microband electrodes, and wherein the exposed surface of each of said microband electrodes has a width less than about 25 micrometers and a thickness less than about 25 micrometers;
- (b) contacting said sample suspected of containing an analyte with said microband electrode array sensor, wherein the lengths of said gaps are each larger than the sum of the lengths of diffusion layers surrounding adjacent microband electrodes formed upon establishing steady state conditions at the surface of each of said microband electrodes, and wherein said microband electrode array sensor generates a steady state signal equal to the sum of the signals produced by each of said microband electrodes when operated independent of said microband electrode array sensor; and
- (c) performing an electrochemical measurement.

15. The method of claim 14 wherein the electrochemical measurement conducted with said sensor is selected from the group consisting of electrogravimetry; controlled-potential coulometry; controlled-current coulometry; voltammetry; anodic- and cathodic-stripping voltammetry; cyclic voltammetry; square wave voltammetry; differential pulse voltammetry; adsorptive stripping voltammetry; potentiometric stripping analysis and amperometry.

16. The method of claim 14 wherein the electrochemical measurement conducted with said sensor is cyclic voltammetry.

17. The method of claim 14 wherein the electrochemical measurement conducted with said sensor is stripping voltammetry.

18. The method of claim 14 wherein said insulating material is selected from the group consisting of silicon carbide, silicon nitride, and silicon dioxide.

19. The method of claim 14 wherein the exposed surface of each of said microband electrodes has a thickness of between about 0.03 and 5 micrometers.

20. The method of claim 14 wherein the exposed surface of each of said microband electrodes has a thickness of between about 0.1 to about 0.2 micrometers.

21. The method of claim 14 wherein the exposed surface of each of said microband electrodes has a width of between 1 and 25 micrometers.

22. The method of claim 14 wherein said microband electrode array sensor further comprises an adhesion layer between said insulating layer and said microband electrodes.

23. The method of claim 22 wherein said adhesion layer comprises chromium.

24. A method of determining the identity, concentration or both of analytes in a sample, said method comprising the steps of:
- contacting a microband electrode array sensor to said sample, said microband electrode array sensor comprising:
  - a substrate having a first edge;
  - a layer of insulating material having a first edge aligned with said first edge of said substrate; and
  - a plurality of microband electrodes between said substrate and said layer of insulating material; said microband electrodes having a surface exposed to said sample at said first edges of said substrate and said insulating layer, said insulating material forming a plurality of gaps of selected lengths, wherein there is one gap positioned between each of two adjacent microband electrodes, wherein the exposed surface of each of said microband electrodes has a width less than about 25 micrometers and a thickness less than about 25 micrometers;
- applying an electric potential to said microband electrode array sensor for a period of time long enough to achieve steady state conditions at the surface of each microband electrode, thereby generating a diffusion layer surrounding each of said microband electrodes;
- selecting said lengths of said gaps such that the lengths of said gaps are each larger than the sum of the lengths of diffusion layers surrounding adjacent microband electrodes upon establishing steady state conditions at the surface of each of said microband electrodes, and
- measuring a steady state current of said microband electrode array sensor, wherein said steady state current of said microband electrode array sensor is equal to the sum of the currents produced by each of said microband electrodes when operated independent of said microband electrode array sensor.

25. The method of claim 24 where said electric potential applied to said microband electrode array sensor is scanned by increasing said electric potential.

26. The method of claim 24 where said electric potential applied to said microband electrode array sensor is scanned by decreasing said electric potential.

27. The method of claim 24 further comprising the step of scanning said electric potential from a negative voltage to a positive voltage.

28. The method of claim 24 further comprising the step of scanning said electric potential from a positive voltage to a negative voltage.

29. The method of claim 24 comprising a method of performing anodic stripping voltammetry, said method further comprising the steps of:
- (a) applying a negative voltage for a sufficient time to allow for an analyte to be reduced onto said microband electrodes, thereby generating plated analyte; and
- (b) scanning the voltage in a positive direction to oxidize said plated analyte off said microband electrodes.

30. The method of claim 24 comprising a method of performing cathodic stripping voltammetry, said method further comprising the steps of:
- (a) applying a positive voltage for a sufficient time to allow for an analyte to be oxidized onto said microband electrodes, thereby generating plated analyte; and
- (b) scanning the voltage in a negative direction to reduce said plated analyte off said microband electrodes.

31. The method of claim 24 wherein said microband electrode array sensor is integrated into a channel.

32. The method of claim 31 wherein said channel is integrated into a flow-through analytical device.

33. The method of claim 24 wherein each of said gaps have lengths greater than 50 micrometers.

34. The method of claim 24 wherein the exposed surface of each of said microband electrodes has a thickness of between about 0.03 micrometers and 5 micrometers.

35. The method of claim 24 wherein the exposed surface of each of said microband electrodes has a width of between about 1 micrometers and about 25 micrometers.

36. The method of claim 24 comprising a method of performing an electrochemical measurement selected from the group consisting of electrogavimetry; controlled-potential coulometry; controlled-current coulometry; voltammetry; anodic- and cathodic-stripping voltammetry; cyclic voltammetry; square wave voltammetry; differential pulse voltammetry; adsorptive stripping voltammetry; potentiometric stripping analysis and amperometry.

* * * * *